(12) United States Patent
Sabetrasekh et al.

(10) Patent No.: US 11,839,354 B2
(45) Date of Patent: Dec. 12, 2023

(54) SYSTEM, APPARATUS, AND METHOD FOR IMAGE-GUIDED LARYNGOSCOPY

(71) Applicants: CHILDREN'S NATIONAL MEDICAL CENTER, Washington, DC (US); Parto Sabetrasekh, Washington, DC (US); Parisa Sabetrasekh, Washington, DC (US); Sam Maghami, Washington, DC (US); Reza Monfaredi, Washington, DC (US); Kevin Cleary, Washington, DC (US)

(72) Inventors: Parto Sabetrasekh, Washington, DC (US); Parisa Sabetrasekh, Washington, DC (US); Sam Maghami, Washington, DC (US); Reza Monfaredi, Washington, DC (US); Kevin Cleary, Washington, DC (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 482 days.

(21) Appl. No.: 16/618,658

(22) PCT Filed: Jun. 5, 2018

(86) PCT No.: PCT/US2018/036071
§ 371 (c)(1),
(2) Date: Dec. 2, 2019

(87) PCT Pub. No.: WO2018/226704
PCT Pub. Date: Dec. 13, 2018

(65) Prior Publication Data
US 2020/0178786 A1  Jun. 11, 2020

Related U.S. Application Data

(60) Provisional application No. 62/515,354, filed on Jun. 5, 2017.

(51) Int. Cl.
*A61B 1/00* (2006.01)
*A61B 1/05* (2006.01)
(Continued)

(52) U.S. Cl.
CPC ...... *A61B 1/00052* (2013.01); *A61B 1/00009* (2013.01); *A61B 1/00073* (2013.01);
(Continued)

(58) Field of Classification Search
CPC ............ A61B 1/00009; A61B 1/00052; A61B 1/00073; A61B 1/00101; A61B 1/00108;
(Continued)

(56) References Cited

U.S. PATENT DOCUMENTS 9,498,112 B1 * 11/2016 Stewart et al.
2011/0077466 A1 * 3/2011 Rosenthal .......... A61B 1/00096
600/188

(Continued)

OTHER PUBLICATIONS

International Search Report and Written Opinion dated Aug. 24, 2018 in PCT/US2018/036071 filed on Jun. 5, 2018.

*Primary Examiner* — Michael J Carey
*Assistant Examiner* — Julianna J Nicolaus
(74) *Attorney, Agent, or Firm* — Oblon, McClelland, Maier & Neustadt, L.L.P.

(57) ABSTRACT

The present disclosure relates to an apparatus and method for intubation. The present disclosure relates to an image-guided laryngoscope comprising a housing having a translational assembly, a primary blade coupled to a distal end of the housing and having a channel, a camera assembly having an image capture device, a display holder coupled to a proximal end of the housing and configured to hold a display, and an endotracheal tube configured to translate within the channel of the primary blade.

20 Claims, 13 Drawing Sheets

(51) Int. Cl.
*A61B 1/267* (2006.01)
*A61M 16/04* (2006.01)
*A61M 25/01* (2006.01)

(52) U.S. Cl.
CPC ............ *A61B 1/00108* (2013.01); *A61B 1/05* (2013.01); *A61B 1/267* (2013.01); *A61M 16/0488* (2013.01); *A61B 1/00016* (2013.01); *A61M 25/0113* (2013.01); *A61M 2205/502* (2013.01)

(58) Field of Classification Search
CPC ....... A61B 1/0016; A61B 1/05; A61B 1/0676; A61B 1/267
See application file for complete search history.

(56) References Cited

U.S. PATENT DOCUMENTS

2011/0178372 A1* 7/2011 Pacey et al.
2012/0186374 A1* 7/2012 Schroeder et al.
2014/0160261 A1* 6/2014 Miller ................ A61B 1/00105
348/77
2015/0059736 A1* 3/2015 Qiu
2016/0206189 A1* 7/2016 Nearman et al.
2018/0147381 A1* 5/2018 Chen ...................... A61B 1/051
2018/0206705 A1* 7/2018 Chan et al.
2018/0221610 A1* 8/2018 Larson ................ A61B 1/0676

* cited by examiner

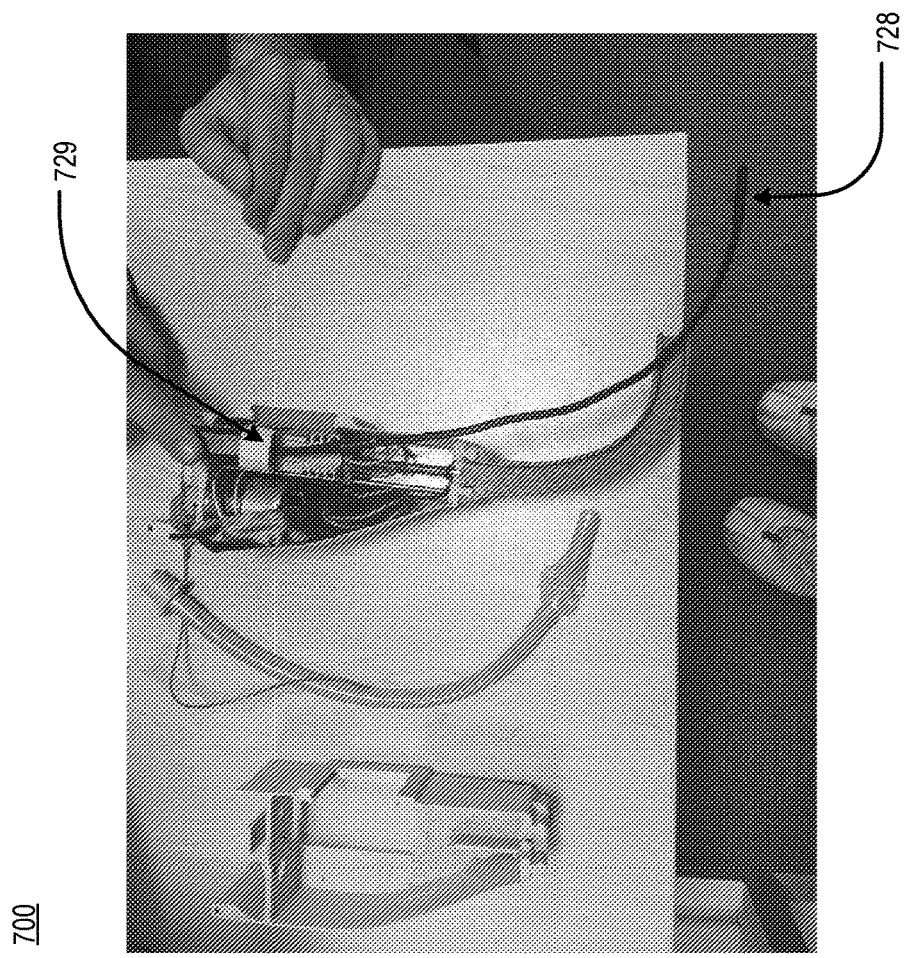
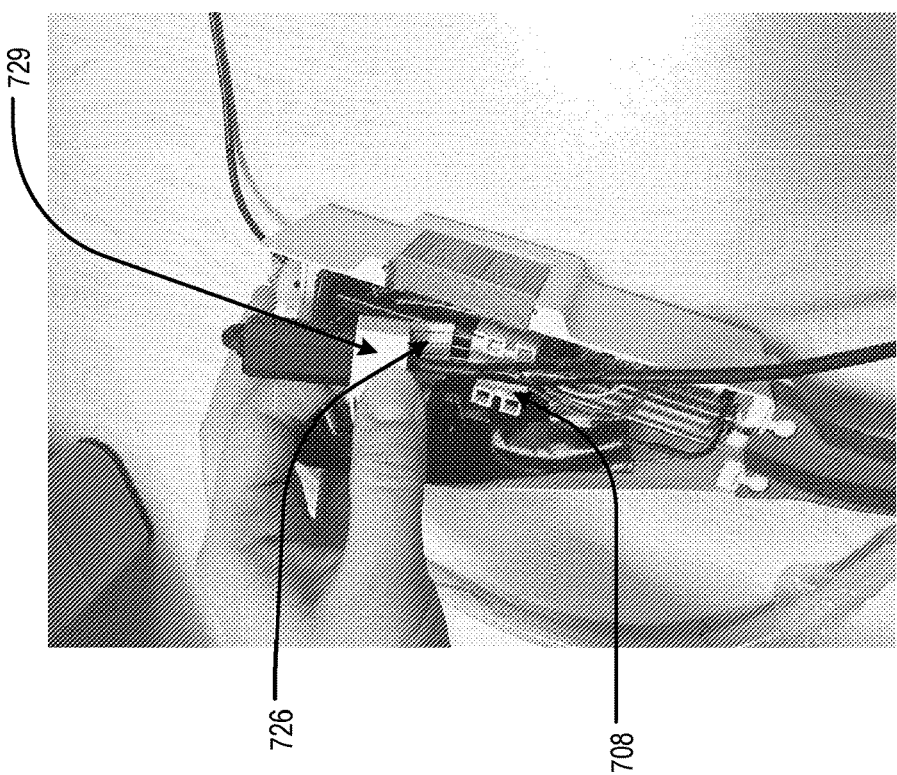
FIG. 7A
FIG. 7B

SYSTEM, APPARATUS, AND METHOD FOR IMAGE-GUIDED LARYNGOSCOPY

CROSS-REFERENCE TO RELATED APPLICATIONS

The present application claims priority to U.S. Provisional Application No. 62/515,354, filed Jun. 5, 2017, the teaching of which is hereby incorporated by reference in its entirety for all purposes.

BACKGROUND

Field of the Disclosure

The present disclosure relates to image-guided laryngoscopy, including systems, apparatuses, and methods thereof.

Description of the Related Art

Intubation, the placement of a flexible plastic tube into the trachea of a patient to maintain an open airway and serve as a conduit, is performed on more than 60 million patients each year in intensive care settings, operating theaters, emergency departments, and trauma bays. In a number of cases, patients suffer serious complications from improper placement of a laryngoscope or endotracheal tube, often causing damage to the tissue linings of the larynx or trachea. In context of the above, speed and accuracy are critical factors for successful, pain-free, intubation. An accessible approach combining these factors has yet to be developed.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to an apparatus and a method of an image-guided laryngoscope.

According to an exemplary embodiment, the present disclosure relates to an image-guided laryngoscope, comprising a housing having a translational assembly including a motor, the housing configured to hold a display coupled to a proximal end thereof, a primary blade coupled to a distal end of the housing and having a channel, a camera assembly having a camera, an endotracheal tube configured to translate within the channel of the primary blade, and processing circuitry configured to receive images from the camera and to control the translational assembly to translate the endotracheal tube within the channel of the primary blade based on processing the received images, wherein the endotracheal tube is coupled to an endotracheal tube carriage, the endotracheal tube carriage being coupled to the translational assembly, wherein the camera is removably provided within a distal end of the endotracheal tube, the camera being in electrical communication with the processing circuitry, the processing circuitry being configured to transmit image information acquired by the camera to the display.

According to an embodiment, the present disclosure is related to a method of laryngoscopy via image-guided laryngoscope, comprising receiving, via processing circuitry, images from a camera of a camera assembly, via processing circuitry, processing, via the processing circuitry, the received images, and translating, via the processing circuitry, an endotracheal tube based upon the processing of the received images, the endotracheal tube being configured to translate within a channel of a primary blade, wherein the endotracheal tube is coupled to an endotracheal tube carriage, the endotracheal tube carriage being coupled to a translational assembly, wherein the primary blade is coupled to a distal end of a housing of the image-guided laryngoscope, the housing comprising the translational assembly including a motor and configured to hold a display coupled to a proximal end thereof, wherein the camera is removably provided within a distal end of the endotracheal tube, the camera being in electrical communication with the processing circuitry, the processing circuitry being configured to transmit image information acquired by the camera to the display.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 7A is a perspective view of a camera assembly of an image-guided laryngoscope, according to an exemplary embodiment of the present disclosure;

FIG. 7B is a side view of a camera assembly of an image-guided laryngoscope, according to an exemplary embodiment of the present disclosure;

DETAILED DESCRIPTION

Figure 1:
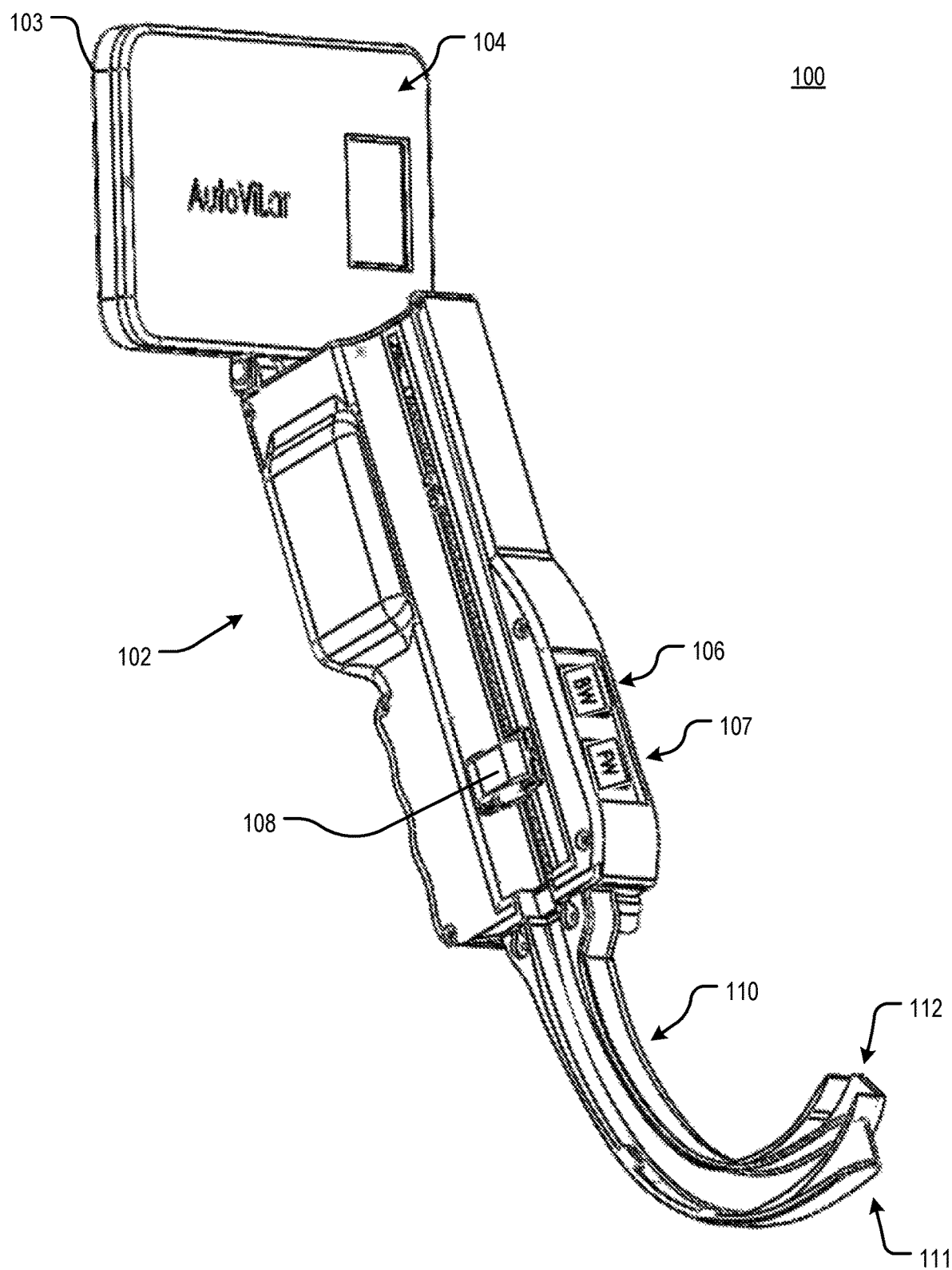
FIG. 1 is a schematic of a perspective view of an image-guided laryngoscope, according to an exemplary embodiment of the present disclosure.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

Tracheal intubation, often referred to simply as intubation, is a procedure by which a flexible plastic tube is inserted through the mouth and larynx, or voice box, of a patient such that the flexible plastic tube is proximate to the tracheal bifurcation. Traditionally, confirmation of proper positioning of the flexible plastic tube is confirmed by radiographs of the chest or auscultation via stethoscope. Successful intubation facilitates ventilation of the lungs of anesthetized patients and prevents asphyxiation via airway obstruction.

Airway management, when the above-described intubation procedure is complicated by obesity, trauma, or edema, for instance, can be one of the greatest challenges for a practitioner performing laryngoscopy. Among several techniques that may be helpful, BURP (Backward-Upward-Rightward Pressure) is a maneuver consisting of backward, upward, and rightward pressure of the larynx. Often, however, regardless of the technique chosen, an intubating practitioner may need to rely on an assisting practitioner, as both hands of the intubating practitioner are dedicated to placement of the laryngoscope and insertion of the endotracheal tube. Specifically, the assisting practitioner focuses on orienting the patient, maintaining pressure on the larynx to improve the view of the glottis, while the intubating practitioner focuses on manipulation of the laryngoscope to guide and position the endotracheal tube.

Recently introduced, video-guided laryngoscopes offer improved vision within the mouth. By positioning an image capture device at a distal end of a blade of the laryngoscope, and connecting the image capture device to a display at a proximal end of the laryngoscope, an intubating practitioner can readily locate and position an endotracheal tube with respect to the glottis of a patient. While providing improved accuracy of endotracheal tube placement with respect to the glottis, these approaches continue to require a plurality of practitioners and fail to provide guidance at the distal end of the trachea, necessitating subsequent confirmation of endotracheal tube positioning via stethoscope or radiograph.

As a result, the present disclosure describes an image-guided laryngoscope providing improved visualization of the internal structures of the laryngotracheal tract while reducing the need for assisting practitioners.

Generally, embodiments of the present disclosure relate to image-guided laryngoscopy, including systems, apparatus, and methods thereof. Further, an image-guided laryngoscope, according to embodiments of the present disclosure, can be preloaded with an endotracheal tube and be configured to provide machine-assisted or automated placement of the endotracheal tube within the trachea. In an embodiment, automated placement of the endotracheal tube may be based on an automatic recognition of various structural features of the larynx and/or trachea based upon an image recognition method.

Turning to the Figures, FIG. 1 is a perspective view of an image-guided laryngoscope, according to an exemplary embodiment of the present disclosure. The image-guided laryngoscope 100 may be comprised of a primary blade 110 coupled to a housing 102, or handle. The housing 102 may be further coupled to a display holder 103 for a display 104. The primary blade 110 may be designed with respect to anatomy of a patient or with respect to generalized anatomy of a specific group, for instance, an age group. There may be a plurality of primary blade 110 configurations according to anatomy. In an embodiment, a second primary blade configuration 112 has a larger curvature than a first primary blade configuration 111, potentially corresponding to a younger age group and an older age group, respectively. An endotracheal (ET) tube may be positioned within an ET tube channel of the primary blade 110 and may be coupled with an ET tube carriage 108 such that a translation assembly can generate a translation of the ET tube. To this end, the ET tube carriage 108 may be further coupled to a lead screw of the translation assembly. In order to control translation of the ET tube, a tactile interface comprising a forward toggle 107 and a reverse toggle 106 may be disposed on a surface of the housing 102.

According to an embodiment, the housing 102, and image-guided laryngoscope 100, generally, may be designed ergonomically such that the housing 102, or handle, is suited to the practitioner. In this context, the design of the housing 102 may vary according to user preference, with the positioning and arrangement of features of the housing 102 varying, therein. In an example, the housing 102 may be substantially rectangular with the tactile interface positioned proximate to the primary blade 110. In another example, the housing 102 may have substantially curved surfaces with the tactile interface positioned proximate to the display holder 103.

According to an embodiment, the housing 102 and primary blade 110 may be fabricated from a material selected from a group including but not limited to polysulfone, polypropylene, polystyrene, and stainless steel such that a variety of primary blade configurations may be readily sterilizable within an operating theater.

According to an embodiment, the forward toggle 107 and the reverse toggle 106 of the tactile interface may be binary switches. In another embodiment, the forward toggle 107 and the reverse toggle 106 may be variable switches responsive to an applied compressive force, wherein an increased compressive force modifies a voltage delivered to a terminal.

According to an embodiment, the forward toggle 107 and the reverse toggle 106 of the tactile interface are coupled to the ET tube carriage 108 via an electric motor of the translation assembly, wherein electrical signals directly modify function of the electric motor. In another embodiment, the translation assembly further comprises a processing circuitry for receiving electrical signals from the tactile interface and controlling the electric motor, therefrom.

Figure 2:
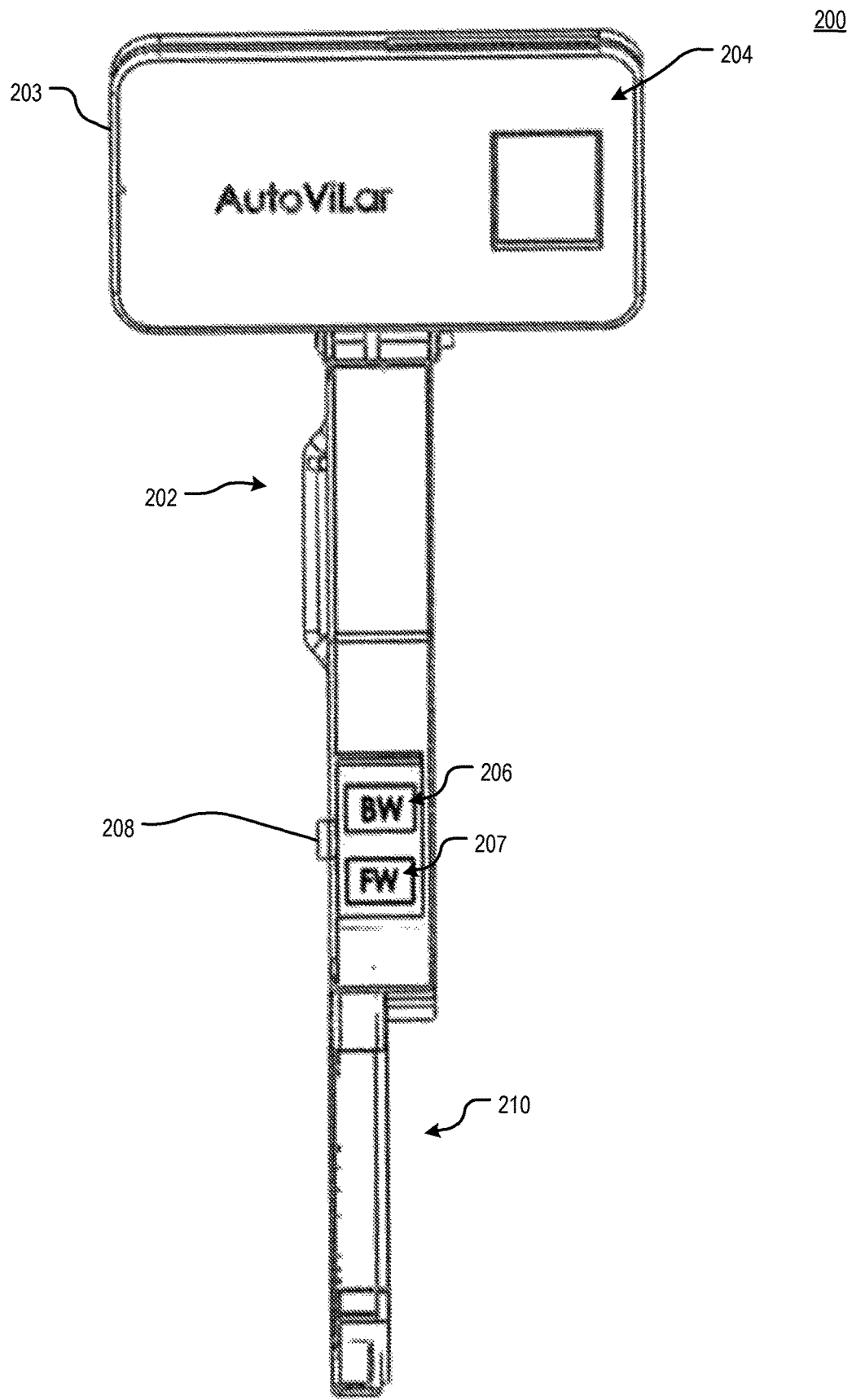
FIG. 2 is a schematic of a rear view of an image-guided laryngoscope, according to an exemplary embodiment of the present disclosure.

FIG. 2 is a rear view of an image-guided laryngoscope, according to an exemplary embodiment of the present disclosure. The image-guided laryngoscope 200 may be comprised of a primary blade 210 coupled to a housing 202, or handle. The housing 202 may be further coupled to a display holder 203 for a display 204. The primary blade 210 may be designed with respect to anatomy of a patient or with respect to generalized anatomy of a specific group, for instance, an age group. An ET tube may be positioned within an ET tube channel of the primary blade 210 and may be coupled with an ET tube carriage 208 such that a translation assembly can generate a translation of the ET tube. To this end, the ET tube carriage 208 may be further coupled to a lead screw of the translation assembly. In order to control translation of the ET tube, a tactile interface comprising a forward toggle 207 and a reverse toggle 206 may be disposed on a surface of the housing 202.

According to an embodiment, the housing 202, and image-guided laryngoscope 200, generally, may be designed ergonomically such that the housing 202, or handle, is suited to the practitioner. In this context, the design of the housing 202 may vary according to user preference, with the positioning and arrangement of features of the housing 202 varying, therein. In an example, the housing 202 may be substantially rectangular with the tactile interface positioned proximate to the primary blade 210. In another example, the housing 202 may have substantially curved surfaces with the tactile interface positioned proximate to the display holder 203.

Figure 3:
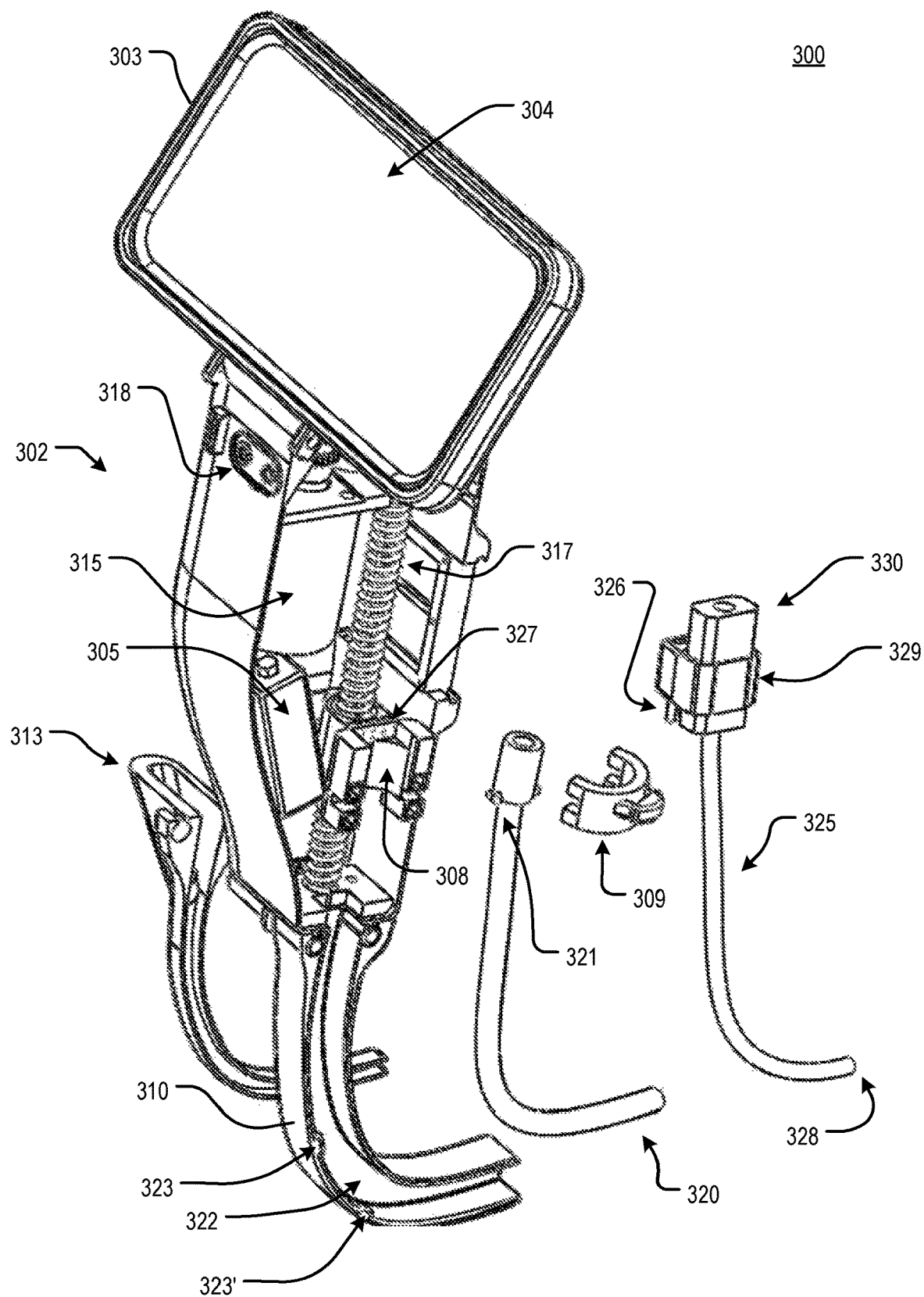
FIG. 3 is a schematic of an expanded, perspective view of an image-guided laryngoscope, according to an exemplary embodiment of the present disclosure.

FIG. 3 is an expanded, perspective view of an image-guided laryngoscope, according to an exemplary embodiment of the present disclosure. The image-guided laryngoscope 300 may be comprised of a primary blade 310 coupled to a housing 302, or handle. The housing 302 may be further coupled to a display holder 303 for a display 304. The primary blade 310 may be designed with respect to anatomy of a patient or with respect to generalized anatomy of a specific group, for instance, an age group. An ET tube 320 may be positioned within an ET tube channel 322 of the primary blade 310 and may be coupled with an ET tube carriage 308 such that a translation assembly may generate a translation of the ET tube 320. An ET tube carriage enclosure 309 allows capture and release of the ET tube 320 from the image-guided laryngoscope 300. One or more ET tube channel flanges 323, 323' ensure the ET tube 320 remains within the ET tube channel 322 during translation into the trachea of a patient. In an embodiment, the ET tube 320 is a flexible plastic fabricated of a material selected from a group including polyvinyl chloride, silicone rubber, or latex rubber. The ET tube 320 may be dimensioned in accordance with patient anatomy or according to generally available sizes, as would be understood by one of ordinary skill in the art.

According to an embodiment of the present disclosure, the translation assembly comprises a power supply 305, an electric motor 315, one or more gears, a lead screw 317, a linear guide, and the ET tube carriage 308 coupled to the lead screw 317. A power supply charging port 318 is disposed on a surface of the housing 302. In an embodiment, the power supply 305 is a rechargeable power supply.

According to an embodiment, the image-guided laryngoscope 300 further comprises a camera assembly including, at least, an image capture device, or, for instance, a camera 328. The camera 328 may be disposed at a distal end of a camera tube 325 of the camera assembly and may be coupled to a camera circuitry 330 disposed at a proximal end of the camera tube 325 of the camera assembly. A processing circuitry within the housing 302, comprising a wireless communication module, may be coupled to the camera 328 via electrical coupling and may be configured to receive and process images from the camera 328. In an embodiment, the camera tube 325 may be a set of wires connecting the camera to the processing circuitry within the housing. The camera circuitry 330 may be further coupled to a camera connector 329 comprising a series of one or more camera connector pins 326. Each of the series of one or more camera connector pins 326 may be configured to couple with a corresponding camera connector port 327 disposed within the ET tube carriage 308. The camera connector 329 positions the camera assembly proximate to the ET tube carriage 308 and the ET tube 320, therein.

According to an embodiment, the camera tube 325, and camera 328 therein, may be configured to fit concentrically within the ET tube 320. An ET tube alignment aid 321, disposed on a proximal end of the ET tube 320, couples to an aspect of the ET tube carriage 308 and ensures a consistent orientation of the ET tube 320 and the camera 328, within. The camera 328, therefore, transmits image information to the processing circuitry within the housing regarding the anatomy surrounding the distal end of the ET tube 320. The processing circuitry within the housing may then transmit, via the wireless communication module, image information to the display 304 in order to visually inform a practitioner of the anatomy at the distal end of the ET tube 320. Understanding the local anatomy surrounding the distal end of the ET tube 320, beyond the distal end of the primary blade 310, allows for accurate and expedient placement of the ET tube 320 within the trachea.

In another embodiment, the wireless communication module of the processing circuitry within the housing transmits image information to an image processing device. The image processing device may be include but is not limited to a user device comprising the display 304 or a remote personal computer. The image processing device may be configured to perform image classification according to an image recognition method. Optionally, the image information can be transmitted wirelessly to another device, such as a mobile electronic device (e.g. cell phone, tablet, etc.), a laptop computer, and/or a personal computer. In an example, the image information can be transmitted directly from the camera assembly, from a processing circuitry associated with the display 304, or from a processing circuitry associated with the image-guided laryngoscope 300, generally, if no such processing circuitry is implemented within the display 304. Optionally, processed data can be used to transmit an electronic signal (e.g., a control signal) back to the image-guided laryngoscope 300 for machine-assisted or automated control of the image-guided laryngoscope 300 in order to, for instance, control forward or reverse toggle operations.

According to an embodiment, the camera 328 may be configured to transmit moving image information in real-time in order to inform a practitioner of current endotracheal conditions. In another embodiment, the camera 328 may be configured to acquire still image information of the laryngotracheal tract and endotracheal conditions. Transmitted moving image information or still image information may be stored to memory resident within the image-guided laryngoscope 300 or within the image processing device (e.g. user device or remote personal computer).

According to an embodiment, the camera assembly may further comprise one or more light sources disposed at the distal end of the ET tube 320 and may be configured to illuminate the laryngotracheal tract, allowing camera 328 function in low or zero 'natural' light situations. In an embodiment, the one or more light sources may be formed integrally with the camera 328. The one or more light sources may be selected from a group including but not limited to light emitting diodes. Alternatively, to this end, the camera 328 may have a night-vision capability to view the trachea in relatively low light settings.

In an embodiment, the one or more light sources may be controlled by the camera circuitry 330 or the processing circuitry within the housing 302, wherein the camera circuitry 330 or the processing circuitry within the housing may be configured to adjust a luminous intensity of the one or more light sources. In another embodiment, the luminous intensity of the one or more light sources may be manually or automatically adjusted based upon an ambient light at the distal end of the ET tube 320. In an example, a luminous intensity of an ambient-light at the distal end of the ET tube 320 is determined by an ambient-light sensor, wherein the luminous intensity of the one or more light sources may be adjusted by the camera circuitry 330, accordingly, in order to provide the highest quality image to the processing circuitry of the housing.

According to an embodiment, following placement of the ET tube 320 within the trachea, the camera 328 and camera tube 325 may be automatically or manually retracted from the ET tube 320. In an example, the camera 328 and camera tube 325, coupled to the camera connector 329, may be decoupled from the ET tube carriage 308 and manually retracted from the ET tube 320.

According to an embodiment, the image-guided laryngoscope 300 further comprises an ancillary blade 313. The ancillary blade 313 may provide a conduit for administration of pharmaceuticals or additional instruments including but not limited to a suction tube.

Figure 4:
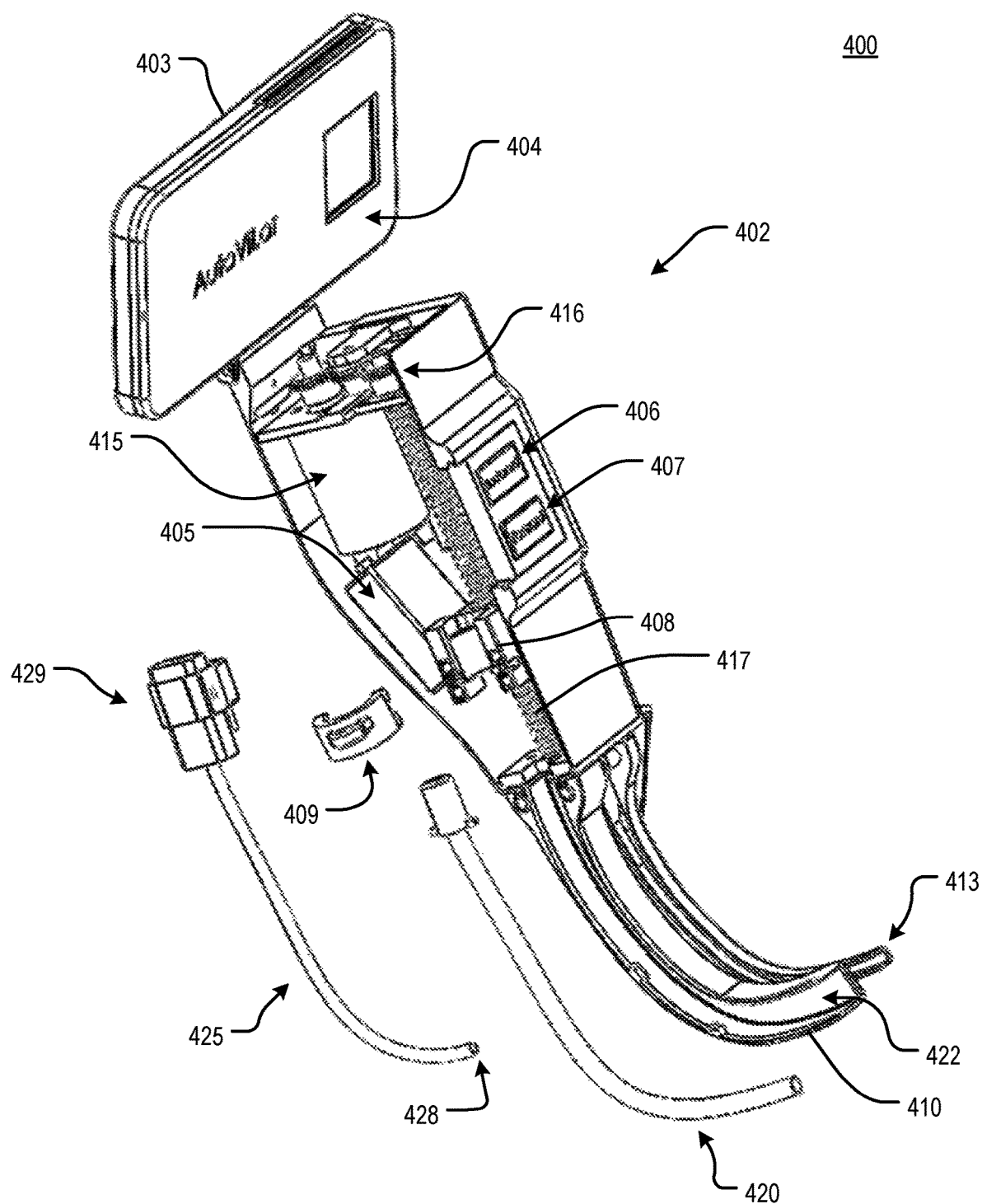
FIG. 4 is a schematic of an expanded, perspective view of an image-guided laryngoscope, according to an exemplary embodiment of the present disclosure.

FIG. 4 is an expanded, perspective view of an image-guided laryngoscope, according to an exemplary embodiment of the present disclosure. The image-guided laryngoscope 400 may be comprised of a primary blade 410 coupled to a housing 402, or handle. The housing 402 may be further coupled to a display holder 403 for a display 404. The primary blade 410 may be designed with respect to anatomy of a patient or with respect to generalized anatomy of a specific group, for instance, an age group. An ET tube 420 may be positioned with an ET tube channel 422 of the primary blade 410 and may be coupled with an ET tube carriage 408 such that a translation assembly can generate a translation of the ET tube 420. An ET tube carriage enclosure 409 allows capture and release of the ET tube 420 from the image-guided laryngoscope 400. In order to control translation of the ET tube 420, a tactile interface comprising a forward toggle 407 and a reverse toggle 406 may be disposed on a surface of the housing 402.

According to an embodiment of the present disclosure, the translation assembly comprises a power supply 405, an electric motor 415, one or more gears 416, a lead screw 417, a linear guide, and the ET tube carriage 408 coupled to the lead screw 417. Following user command by a practitioner via the forward toggle 407 and reverse toggle 406 of the tactile interface, rotational energy of the electric motor 415 is converted to translational energy via the lead screw 417, coupled to the electric motor 415 via the one or more gears 416. In an embodiment, the power supply 405 is a rechargeable power supply.

According to an embodiment, the image-guided laryngoscope 400 further comprises a camera assembly including an image capture device, or, for instance, a camera 428. The camera 428 may be disposed at a distal end of a camera tube 425 of the camera assembly and may be coupled to a camera circuitry disposed at a proximal end of the camera tube 425 of the camera assembly. A processing circuitry within the housing 402, comprising a wireless communication module, may be coupled to the camera 428 via electrical coupling and may be configured to receive and process images from the camera 428. In an embodiment, the camera tube 425 may be a set of wires connecting the camera to the processing circuitry within the housing. The camera circuitry may be further coupled to a camera connector 429 comprising a series of one or more camera connector pins, each of the series of one or more camera connector pins being configured to couple with a corresponding camera connector port disposed within the ET tube carriage 408. The camera connector 429 positions the camera assembly proximate to the ET tube carriage 408 and the ET tube 420, therein.

According to an embodiment, the image-guided laryngoscope 400 further comprises an ancillary blade 413. The ancillary blade 413 may provide a conduit for administration of pharmaceuticals or additional instruments including but not limited to a suction tube.

According to an embodiment, the housing 402, and image-guided laryngoscope 400, generally, may be designed ergonomically such that the housing 402, or handle, is suited to the practitioner. In this context, the design of the housing 402 may vary according to user preference, with the positioning and arrangement of features of the housing 402 varying, therein. In an example, the housing may be substantially rectangular with the tactile interface positioned proximate to the primary blade. In another example, as shown in FIG. 4, the housing 402 may have substantially curved surfaces with the tactile interface positioned proximate to the display holder 403.

Figure 5:
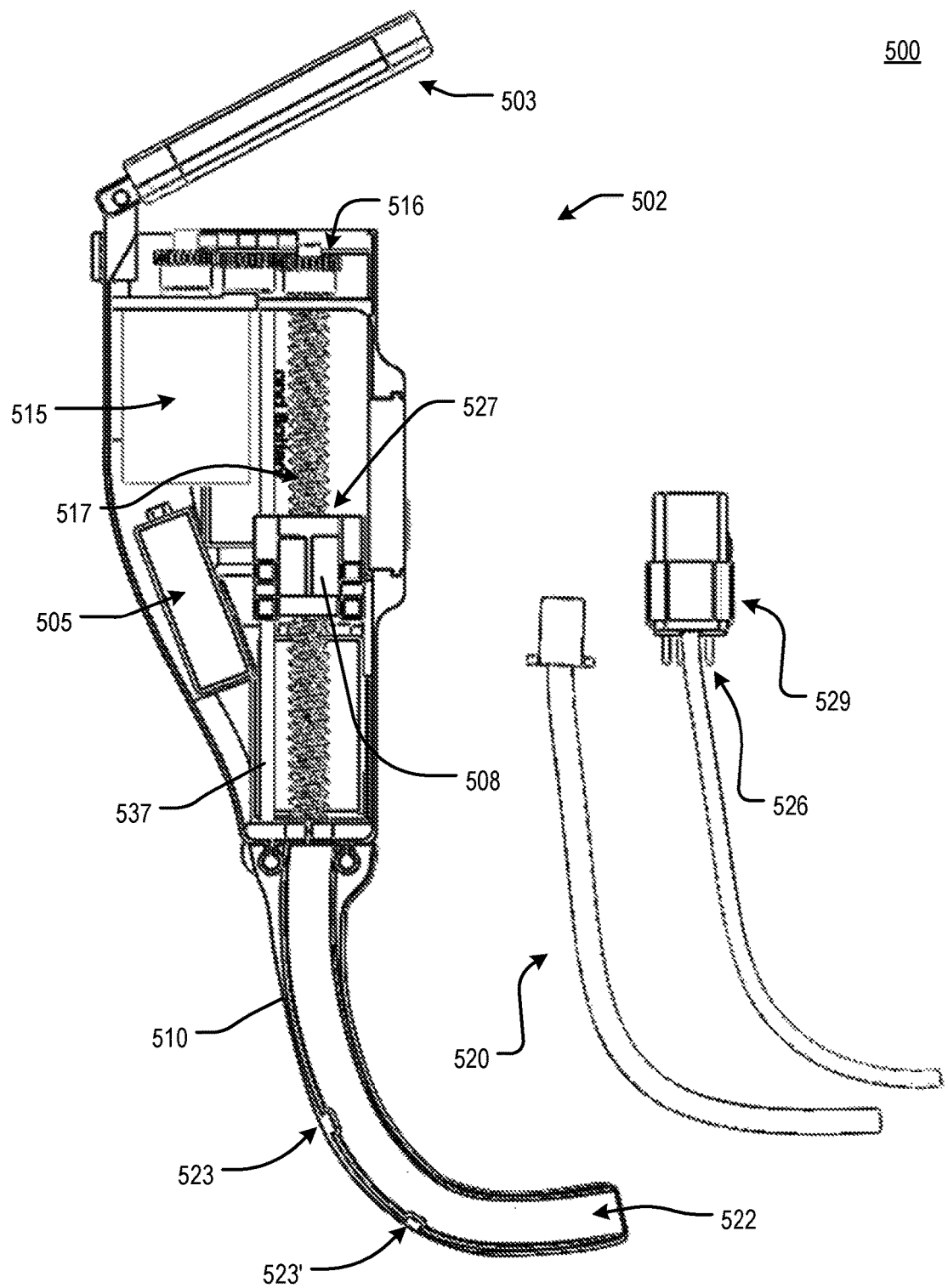
FIG. 5 is a schematic of an expanded, side view of an image-guided laryngoscope, according to an exemplary embodiment of the present disclosure.

FIG. 5 is an expanded, side view of an image-guided laryngoscope, according to an exemplary embodiment of the present disclosure. The image-guided laryngoscope 500 may be comprised of a primary blade 510 coupled to a housing 502, or handle. The housing 502 may be further coupled to a display holder 503 for a display. The primary blade 510 may be designed with respect to anatomy of a patient or with respect to generalized anatomy of a specific group, for instance, an age group. An ET tube 520 may be positioned with an ET tube channel 522 of the primary blade 510 and may be coupled with an ET tube carriage 508 such that a translation assembly can generate a translation of the ET tube 520. One or more ET tube channel flanges 523, 523' ensure the ET tube 520 remains within the ET tube channel 522 during translation into the trachea of a patient.

According to an embodiment, the image-guided laryngoscope 500 further comprises a camera assembly including an image capture device, or, for instance, a camera. The camera may be disposed at a distal end of a camera tube of the camera assembly and may be coupled to a camera circuitry disposed at a proximal end of the camera tube of the camera assembly. A processing circuitry within the housing 502, comprising a wireless communication module, may be coupled to the camera via electrical coupling and may be configured to receive and process images from the camera. In an embodiment, the camera tube may be a set of wires connecting the camera to the processing circuitry within the housing. The camera circuitry may be further coupled to a camera connector 529 comprising a series of one or more camera connector pins 526. Each of the series of one or more camera connector pins 526 may be configured to couple with a corresponding camera connector port 527 disposed within the ET tube carriage 508. The camera connector 529 positions the camera assembly proximate to the ET tube carriage 508 and the ET tube 520, therein. According to an embodiment, the camera tube may be configured to fit concentrically within the ET tube 520.

According to an embodiment of the present disclosure, the translation assembly comprises a power supply 505, an electric motor 515, one or more gears 516, a lead screw 517, a linear guide 537, and the ET tube carriage 508 coupled to the lead screw 517. Following user command by a practitioner via the tactile interface, rotational energy of the electric motor 515 is converted to translational energy via the lead screw 517, coupled to the electric motor 515 via the one or more gears 516.

In an embodiment, the power supply 505 may be a rechargeable power supply selected from a group including but not limited to nickel-metal hydride batteries, lithium-ion batteries, and lithium-ion polymer batteries. In an embodiment, the electric motor 515 may be selected from a group including but not limited to brushed direct current (DC) motors, brushless DC motors, servomotors, and voice-coil motors.

According to an embodiment, translation of the ET tube 520, and camera tube, therein, within the ET tube channel of the primary blade 510 may be achieved by linear translation of the ET tube carriage 508 via screw mechanism. In an example, the ET tube carriage 508 is coupled to the lead screw 517 via nut. The ET tube carriage 508 is further constrained by a linear guide 537 passing through an aspect of the ET tube carriage 508 such that rotation of the ET tube carriage 508 about the long axis of the lead screw 517 is impossible.

In an example, the electric motor 515 may be coupled to a proximate one of the one or more gears 516. Subsequently, rotational energy is transferred between each of the one or more gears 516. A remote one of the one or more gears 516, coupled to the lead screw 517, transfers the rotational energy to the lead screw 517. The nut coupled to the ET tube carriage 508 and constrained by the linear guide 537, linearly translates along the long axis of the lead screw 517 in accordance with the orientation of rotation (e.g. clockwise or counterclockwise). Responsive to a user command, the above-described mechanism allows a practitioner to controllably translate an ET tube 520 within the trachea of a patient.

Figure 6:
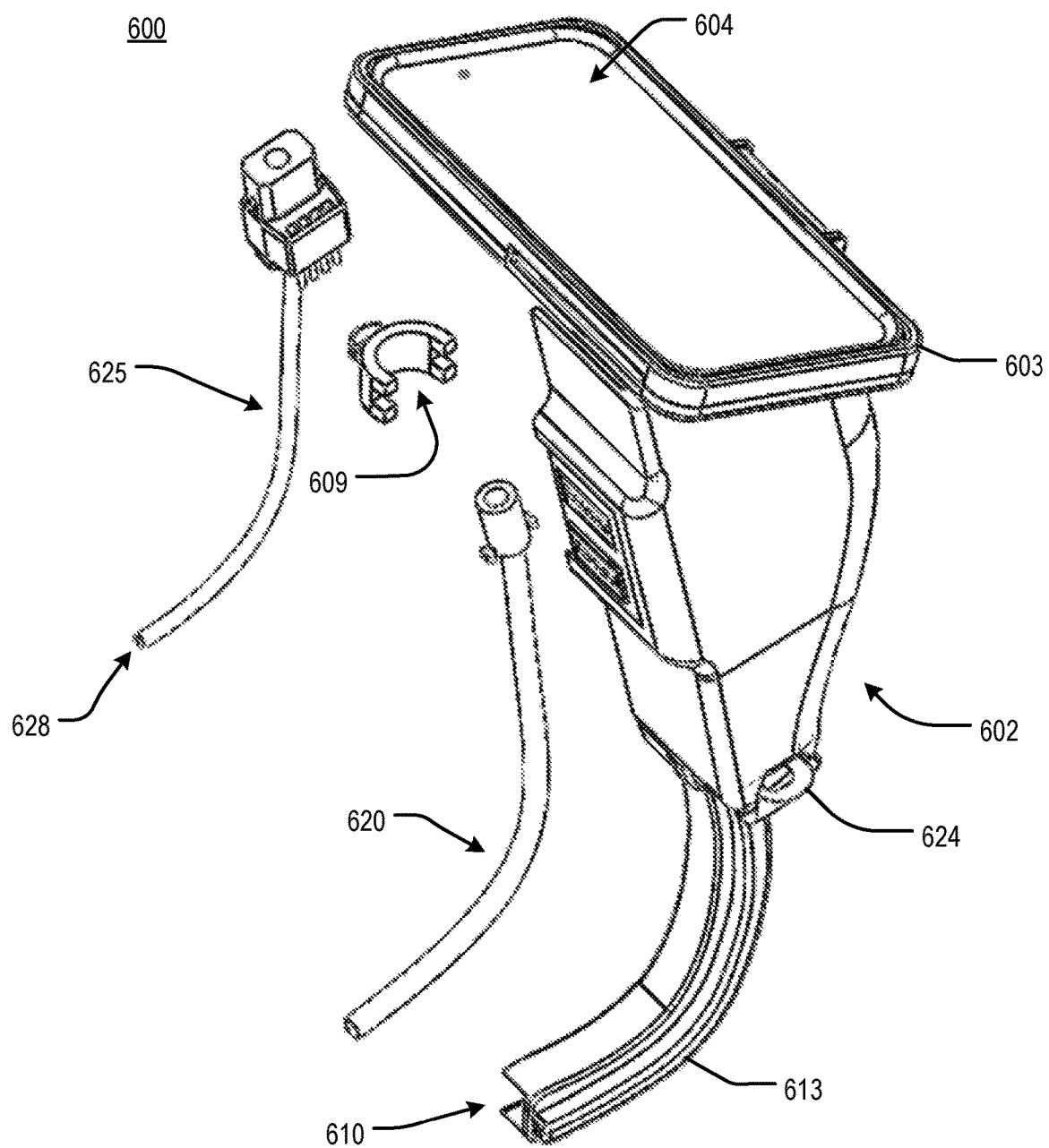
FIG. 6 is a schematic of an expanded, perspective view of an image-guided laryngoscope, according to an exemplary embodiment of the present disclosure.

FIG. 6 is an expanded, perspective view of an image-guided laryngoscope, according to an exemplary embodiment of the present disclosure. The image-guided laryngoscope 600 may be comprised of a primary blade 610 coupled to a housing 602, or handle. The housing 602 may be further coupled to a display holder 603 for a display 604. The primary blade 610 may be designed with respect to anatomy of a patient or with respect to generalized anatomy of a specific group, for instance, an age group. An ET tube 620 may be positioned with an ET tube channel of the primary blade 610 and may be coupled with an ET tube carriage such that a translation assembly can generate a translation of the ET tube 620. An ET tube carriage enclosure 609 allows capture and release of the ET tube 620 from the image-guided laryngoscope 600.

According to an embodiment, the image-guided laryngoscope 600 further comprises a camera assembly including an image capture device, or, for instance, a camera 628. The camera 628 may be disposed at a distal end of a camera tube 625 of the camera assembly and be coupled to a camera circuitry disposed at a proximal end of the camera tube 625 of the camera assembly. In another embodiment, the camera assembly includes a processing circuitry within the housing 602, comprising a wireless communication module, which may be coupled to the camera 628 via electrical coupling and may be configured to receive and process images from the camera 628.

According to an embodiment, the image-guided laryngoscope 600 further comprises an ancillary blade 613. The ancillary blade 613 may provide a conduit for administration of pharmaceuticals or additional instruments including but not limited to a suction tube. An ancillary blade tube coupling 624 may be disposed at a distal end of the housing 602 of the image-guided laryngoscope 600 such that an ancillary tube may be positioned within the ancillary blade 613. The position of the ancillary tube may be manually adjusted with respect to the patient or may be connected to a secondary translation assembly for machine-assisted movement.

FIG. 7A and FIG. 7B are a perspective view of a camera assembly of an image-guided laryngoscope, according to an exemplary embodiment of the present disclosure. Specifically, FIG. 7A reflects initiation of an installation procedure of the camera assembly in the image-guided laryngoscope 700. A camera tube, connecting a camera at a distal end of the camera tube with a camera circuitry at a proximal end of the camera tube, is coupled to a camera connector 729. The camera connector 729 comprises a series of one or more camera connector pins 726. During assembly of the image-guided laryngoscope 700, the series of one or more camera connector pins 726 are coupled with a corresponding series of one or more connector ports disposed within an ET tube carriage 708. FIG. 7B illustrates the disposition of the camera connector 729 with respect to the ET tube carriage and the housing of the image-guided laryngoscope 700. Once the series of one or more camera connector pins have been coupled with the corresponding series of one or more camera connector ports, the image-guided laryngoscope is prepared for use.

According to an embodiment, prior to coupling of the camera assembly to the translation assembly, as described above, the camera tube of the camera assembly is positioned concentrically within an ET tube such that a camera 728 of the camera assembly is distally positioned with the ET tube.

Figure 8B:
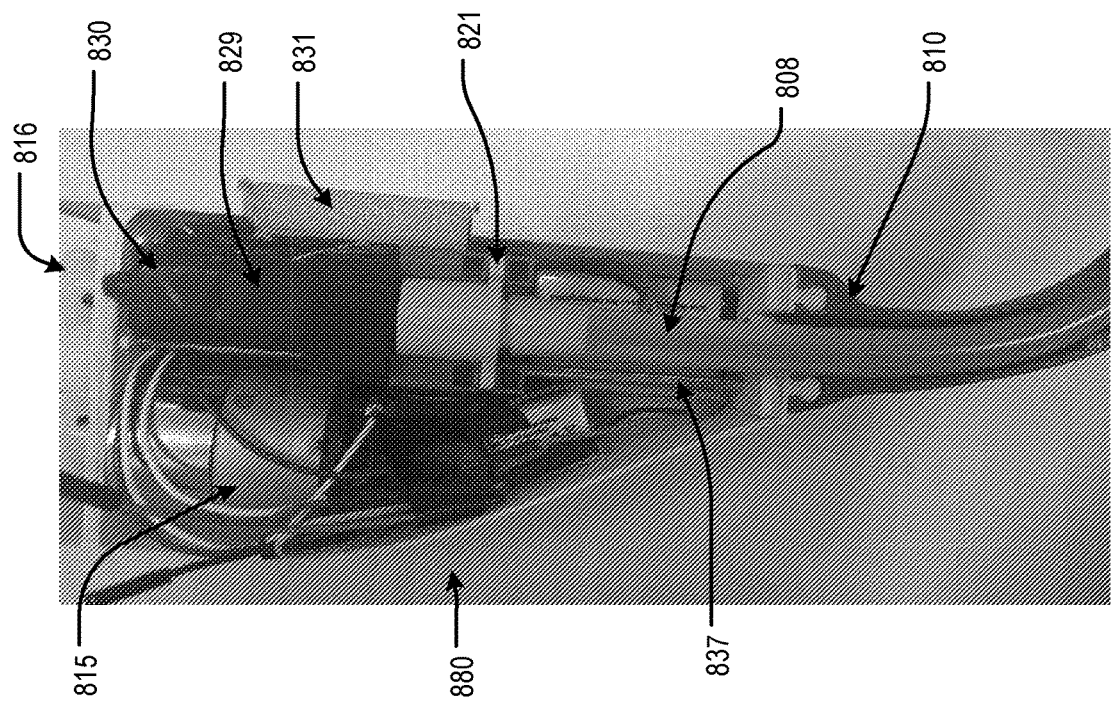
FIG. 8B is a side view of a translation assembly of an image-guided laryngoscope, according to an exemplary embodiment of the present disclosure.
Figure 8A:
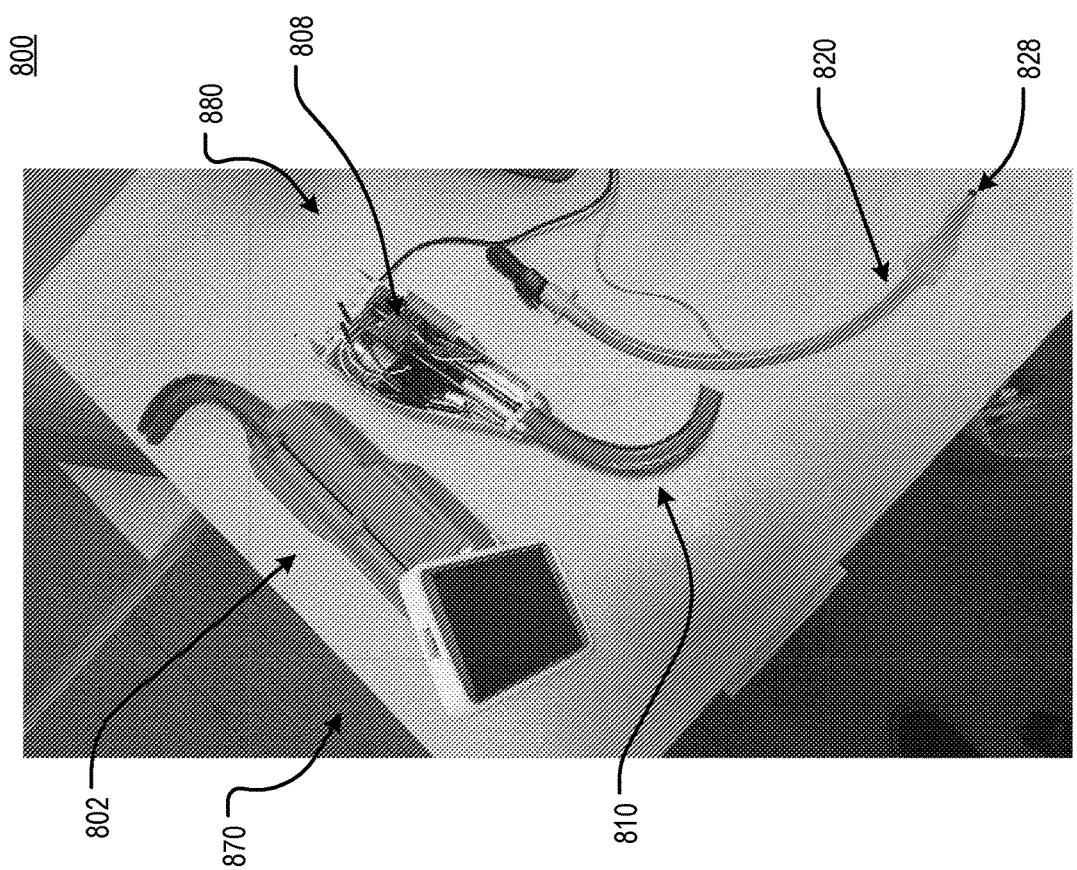
FIG. 8A is a side view of an image-guided laryngoscope, according to an exemplary embodiment of the present disclosure.

To this end, FIG. 8A and FIG. 8B are a side view of an image-guided laryngoscope, according to an exemplary embodiment of the present disclosure. FIG. 8A illustrates an image-guided laryngoscope 800 comprising a housing 802, a primary blade 810, and a camera tube including a camera 828 therein, positioned within an ET tube 820. During installation, as described in FIG. 7A and FIG. 7B, the camera assembly and ET tube 820 may be coupled with an ET tube carriage 808 of the housing 802 such that an ET tube alignment aid may be fitted to a corresponding aspect of the ET tube carriage 808. FIG. 8B illustrates the camera assembly and ET tube following installation. According to an embodiment, the ET tube alignment aid 821 may be fitted with the corresponding aspect of the ET tube carriage 808. A distal aspect of the ET tube may reside within an ET tube channel of the primary blade 810. The camera assembly, comprising a camera connector 829 coupled to a camera circuitry 830, may be coupled to the ET tube carriage 808 via camera connector pins and corresponding camera connector ports. In another embodiment, the camera assembly includes a processing circuitry within the housing 802, comprising a wireless communication module, which may be coupled to the camera 628 via electrical coupling and may be configured to receive and process images from the camera 628.

During translation, the translation assembly, comprising an electric motor 815 and one or more gears 816, converts rotational energy to translational energy. With rotation of a lead screw, the ET tube carriage 808, rotationally constrained by a linear guide 837, translates along a long axis of the lead screw. This translation is responsive to user command via a tactile interface 831. User commands, informed by image information delivered to a display of the image-guided laryngoscope 800, result in translation of the ET tube and camera, therein, within the trachea of a patient.

According to an embodiment, an ET tube alignment aid, coupled to the ET tube carriage 808, provides a surface against which a translational force is applied by the translation assembly.

According to an embodiment, the housing 802, and image-guided laryngoscope 800, generally, may be designed ergonomically such that the housing 802, or handle, is suited to the practitioner, as illustrated in FIG. 8A. In this context, the design of the housing 802 may vary according to user preference, with the positioning and arrangement of features of the housing 802 varying, therein. In an example, the housing may be substantially rectangular 870 with the tactile interface positioned proximate to the primary blade. In another example, as shown in FIG. 8A, the housing 802 may have substantially curved surfaces 880 with the tactile interface positioned proximate to the display holder.

Figure 9:
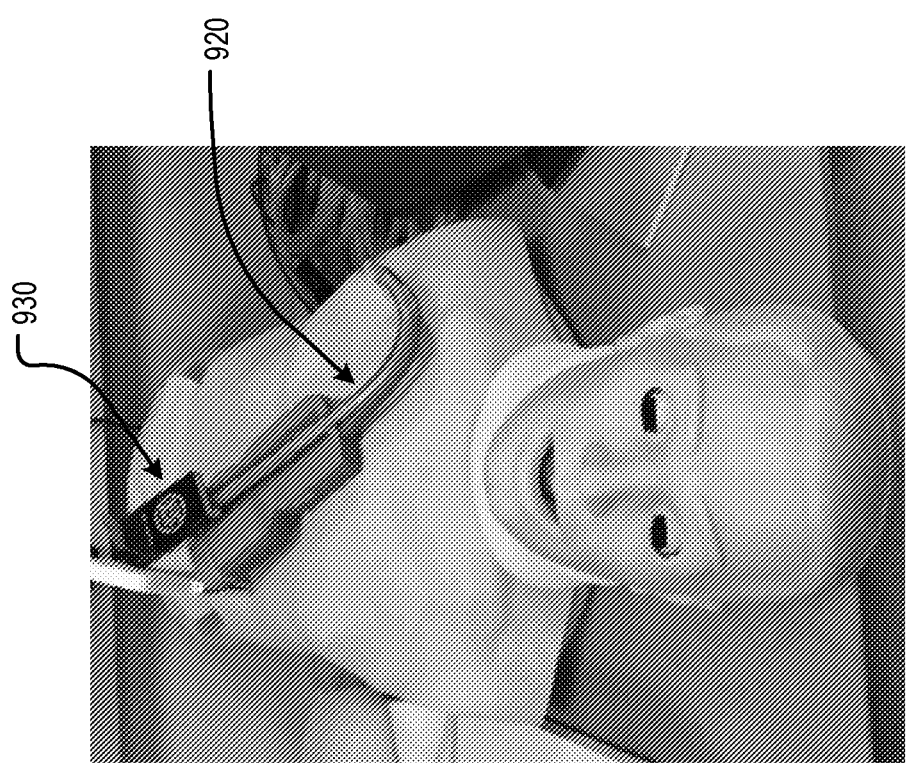
FIG. 9 is a perspective view of an image-guided laryngoscope in a simulated setting, according to an exemplary embodiment of the present disclosure.

FIG. 9 is a perspective view of an image-guided laryngoscope in a simulated setting, according to an exemplary embodiment of the present disclosure. The image-guided laryngoscope 900 has a substantially rectangular shape, according to an ergonomic request of a user, or practitioner. A camera circuitry 930, coupled to a camera connector, camera tube, and camera, is visible at a proximal aspect of an ET tube 920. In an embodiment, during intubation, image information collected by the camera at a distal end of the camera tube may be transmitted via a wireless communication module of the processing circuitry within the housing to a display of a user device.

According to an embodiment, the image-guided laryngoscope 900 may be operated with a single hand of a practitioner, informed by endotracheal image information displayed on the user device, allowing for physical manipulation of a head, and larynx therein, of a patient with a second hand.

Figure 10:
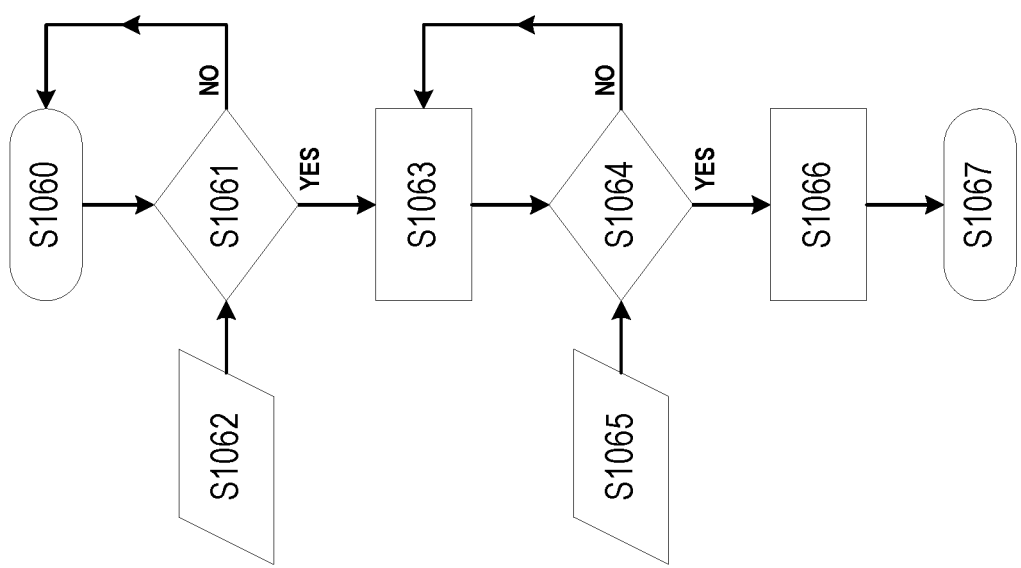
FIG. 10 is a flowchart of an intubation process via an image-guided laryngoscope, according to an exemplary embodiment of the present disclosure.

The intubation process, according to an exemplary embodiment of the present disclosure, is described in FIG. 10, a flowchart of an intubation process via an image-guided laryngoscope. In an embodiment, an image-guided laryngoscope is selected according to patient anatomy, with appropriate primary blade curvature and ET tube dimensions, therein. In another embodiment, the selected image-guided laryngoscope is provided with an appropriate ET tube preloaded.

Initially, the image-guided laryngoscope may be appropriately positioned proximate the larynx of a patient S1060. If it is determined, via image information acquired S1062 by a camera at a distal end of the ET tube and displayed via a display of a user device, the image-guided laryngoscope is positioned proximate the glottis S1061, translation of the ET tube into the trachea of the patient may commence. Alternatively, the distal end of a primary blade of the image-guided laryngoscope must be repositioned in order to be proximate the glottis. Once positioned proximate the glottis, the ET tube may be advanced S1063 via a translation assembly. Informed by the image information acquired S1065 by the camera and displayed on the display of the user device, it may be determined S1064 if the distal end of the ET tube is positioned appropriately relative to the bifurcation of the trachea. If it is determined that the distal end of the ET tube is positioned appropriately, the camera may be removed from the distal end of the ET tube and the camera assembly may be removed from the image-guided laryngoscope S1066. Alternatively, image information acquired by the camera continues to inform movement of the translation assembly to position the distal end of the ET tube relative to the bifurcation of the trachea. Once positioned, and the camera has been removed, the ET tube may be decoupled from the image-guided laryngoscope S1067 and prepared for ventilation.

In an embodiment, the translation assembly may be controlled by user command via a tactile interface. In another embodiment, the translation assembly is controlled by a local or remote processing circuitry coupled, via wired or wireless connection, to the camera of a camera assembly. In an example, the local or remote processing circuitry is an image processing device, wherein image information acquired by the camera is identified and evaluated in order to inform a subsequent movement of the translation assembly.

The image information processing device may be configured to identify objects of the image information and determine a motion of the translation assembly, accordingly. In an example, the image information processing device employs an image recognition method selected from a group of machine learning approaches including but not limited to support vector machine, neural networks or logistic regression. The image information processing device may comprise a classifier trained to identify, or predict, biological structures including but not limited to the epiglottis, the glottis, the vocal cords, the cricoid cartilage, or the bifurcation of the trachea into bronchi. During operation, recognition and identification of biological structures, such as the vocal cords, may guide the translation of the ET tube into the trachea. Moreover, in an exemplary embodiment, final positioning of the distal aspect of the ET tube may be determined and controlled via image recognition of the bifurcation of the trachea by the image processing device. It should be appreciated that a variety of methods for image recognition may be employed in the above-described process.

According to an embodiment, in addition to image information acquired via the camera, the ET tube or camera assembly may be outfitted with a tactile sensor. The tactile sensor may be configured to sense tracheal tissue contact and prevent excess trauma. The tactile sensor may transmit tactile information to a processing circuitry within the housing via the wireless processing circuitry of the camera assembly, to the user device having the display, or to a remote personal computer. Further, the tactile sensor may be one of a variety of tactile sensors employing sensors including but not limited to piezoresistive, piezoelectric, capacitive, and elastoresistive sensors.

In another embodiment, the tactile sensor is configured to determine contact with, or proximity to, relevant biological structures or landmarks including the epiglottis, vocal cords, and cartilage rings of the trachea. Similar to the image recognition methods employed previously for object identification, machine learning approaches may be applied to the evaluation of acquired tactile sensor data. A classifier may be trained on a reference database including a mapping of a variety of normal human anatomy of the larynx and trachea and can be constructed to contain data relevant to patients of different physical size. In this way, the classifier can predict a classification of a sensation measured by the tactile sensor (e.g., glottis, tracheal cartilage, etc.) and provide guidance to the translational assembly, accordingly. In an example, the guidance may include a reverse toggle instruction to remove the distal end of the ET tube from a bronchus of the lungs.

According to an embodiment, user commands of the movement of the translation assembly may be verbal commands. The verbal commands may be received by a speaker of a user device, processed by resident processing circuitry, and transmitted to the translation assembly of the image-guided laryngoscope via wireless communication.

According to an embodiment, user commands of the movement of the translation assembly may be tactile commands delivered to a display of a user device. The tactile commands may be received by the display of the user device, processed by resident processing circuitry, and transmitted to the translation assembly of the image-guided laryngoscope via wireless communication.

Figure 11:
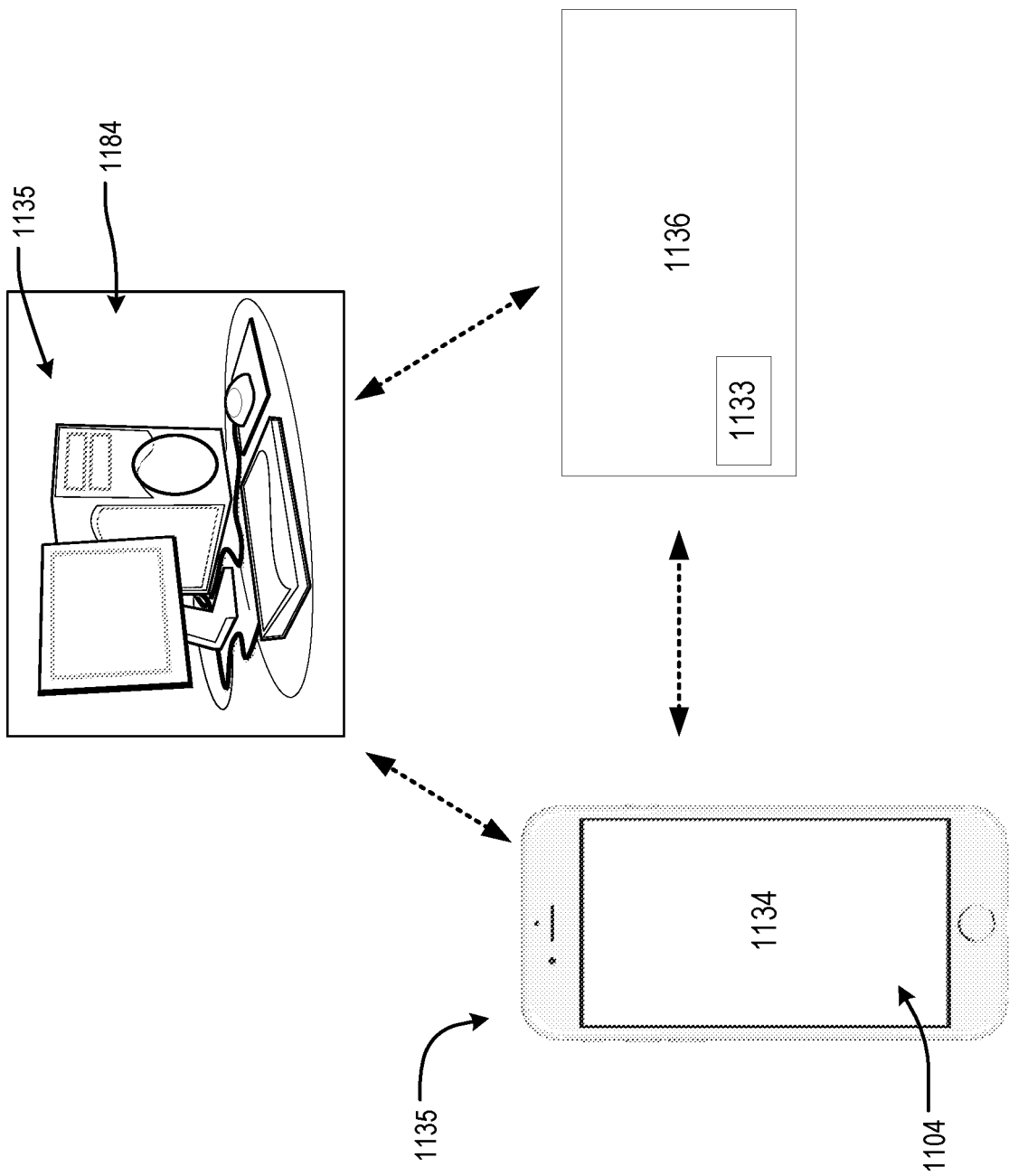
FIG. 11 is a schematic of wireless communication between a camera assembly and one or more image processing devices of an image-guided laryngoscope, according to an exemplary embodiment of the present disclosure.

FIG. 11 is a schematic of wireless communication between a camera assembly and one or more image processing devices of an image-guided laryngoscope, according to an exemplary embodiment of the present disclosure. In an embodiment, a processing circuitry within a housing 1136, comprising a wireless communications module 1133, may be configured to transmit information with a display 1104 of a user device 1134. In another embodiment, the processing circuitry within the housing 1136, via the wireless communications module 1133, may be configured to transmit information to and between an image processing device 1135. In an embodiment, the wireless communication module is an IEEE 802.11 b/g compliant WiFi module with an embedded IPv4 TCP/IP stack with an SPI host interface at 16 MHz. In an example, the image processing device may be the user device 1134 or a remote personal computer 1184. In another embodiment, the image processing device 1135 may be a remote server.

According to an embodiment, the transmitted information may be image information or tactile information. In another embodiment, image information acquired by a camera of a camera assembly or tactile information acquired by a tactile sensor may be transmitted via wired communication.

Figure 12:
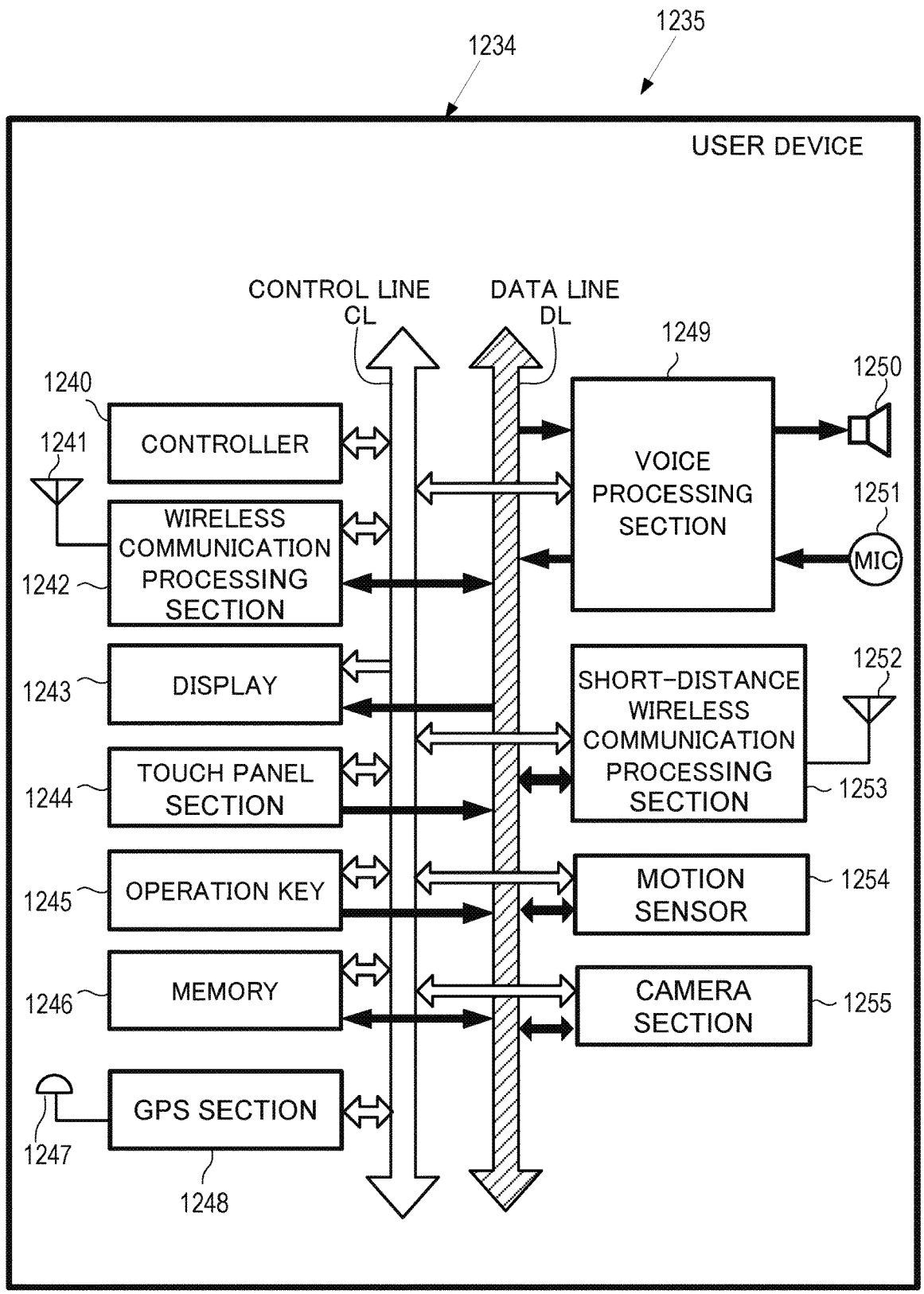
FIG. 12 is a hardware schematic of an image processing device, according to an exemplary embodiment of the present disclosure.

FIG. 12 is a detailed block diagram illustrating an exemplary image processing device, according to an embodiment of the present disclosure. In an embodiment, the image processing device 1235 is a user device 1234. In certain embodiments, user device 1234 may be a smartphone. However, the skilled artisan will appreciate that the features described herein may be adapted to be implemented on other devices (e.g., a laptop, a tablet, a server, an e-reader, a camera, a navigation device, etc.). The exemplary user device 1234 includes a controller 1240 and a wireless communication processor 1242 connected to an antenna 1241. A speaker 1250 and a microphone 1251 are connected to a voice processor 1249.

The controller 1240 may include one or more Central Processing Units (CPUs), and may control each element in the user device 1234 to perform functions related to communication control, audio signal processing, control for the audio signal processing, still and moving image processing and control, and other kinds of signal processing. The controller 1240 may perform these functions by executing instructions stored in a memory 1246. Alternatively or in addition to the local storage of the memory 1246, the functions may be executed using instructions stored on an external device accessed on a network or on a non-transitory computer readable medium.

The memory 1246 includes but is not limited to Read Only Memory (ROM), Random Access Memory (RAM), or a memory array including a combination of volatile and non-volatile memory units. The memory 1246 may be utilized as working memory by the controller 1240 while executing the processes and algorithms of the present disclosure. Additionally, the memory 1246 may be used for long-term storage, e.g., of image data and information related thereto. The memory 1246 may be configured to store the battle view information, operation view information and list of commands.

The user device 1234 includes a control line CL and data line DL as internal communication bus lines. Control data to/from the controller 1240 may be transmitted through the control line CL. The data line DL may be used for transmission of voice data, display data, etc.

The antenna 1241 transmits/receives electromagnetic wave signals between base stations for performing radio-based communication, such as the various forms of cellular telephone communication. The wireless communication processor 1242 controls the communication performed between the user device 1234 and other external devices via the antenna 1241. For example, the wireless communication processor 1242 may control communication between base stations for cellular phone communication.

The speaker 1250 emits an audio signal corresponding to audio data supplied from the voice processor 1249. The microphone 1251 detects surrounding audio and converts the detected audio into an audio signal. The audio signal may then be output to the voice processor 1249 for further processing. The voice processor 1249 demodulates and/or decodes the audio data read from the memory 1246 or audio data received by the wireless communication processor 1242 and/or a short-distance wireless communication processor 1253. Additionally, the voice processor 1249 may decode audio signals obtained by the microphone 1251.

The exemplary user device 1234 may also include a display 1243, a touch panel 1244, an operation key 1245, and a short-distance communication processor 1253 connected to an antenna 1252. The display 1243 may be a Liquid Crystal Display (LCD), an organic electroluminescence display panel, or another display screen technology. In addition to displaying still and moving image data, the display 1243 may display operational inputs, such as numbers or icons which may be used for control of the user device 1234. The display 1243 may additionally display a GUI for a user to control aspects of the user device 1234 and/or other devices. Further, the display 1243 may display characters and images received by the user device 1234 and/or stored in the memory 1246 or accessed from an external device on a network. For example, the user device 1234 may access a network such as the Internet and display text and/or images transmitted from a Web server.

The touch panel 1244 may include a physical touch panel display screen and a touch panel driver. The touch panel 1244 may include one or more touch sensors for detecting an input operation on an operation surface of the touch panel display screen. The touch panel 1244 also detects a touch shape and a touch area. Used herein, the phrase "touch operation" refers to an input operation performed by touching an operation surface of the touch panel display with an instruction object, such as a finger, thumb, or stylus-type instrument. In the case where a stylus or the like is used in a touch operation, the stylus may include a conductive material at least at the tip of the stylus such that the sensors included in the touch panel 1244 may detect when the stylus approaches/contacts the operation surface of the touch panel display (similar to the case in which a finger is used for the touch operation). One or more of the display 1243 and the touch panel 1244 are examples of a touch panel display.

In certain aspects of the present disclosure, the touch panel 1244 may be disposed adjacent to the display 1243 (e.g., laminated) or may be formed integrally with the display 1243. For simplicity, the present disclosure assumes the touch panel 1244 is formed integrally with the display 1243 and therefore, examples discussed herein may describe touch operations being performed on the surface of the display 1243 rather than the touch panel 1244. However, the skilled artisan will appreciate that this is not limiting.

For simplicity, the present disclosure assumes the touch panel 1244 is a capacitance-type touch panel technology. However, it should be appreciated that aspects of the present disclosure may easily be applied to other touch panel types (e.g., resistance-type touch panels) with alternate structures. In certain aspects of the present disclosure, the touch panel 1244 may include transparent electrode touch sensors arranged in the X-Y direction on the surface of transparent sensor glass.

The touch panel driver may be included in the touch panel 1244 for control processing related to the touch panel 1234, such as scanning control. For example, the touch panel driver may scan each sensor in an electrostatic capacitance transparent electrode pattern in the X-direction and Y-direction and detect the electrostatic capacitance value of each sensor to determine when a touch operation is performed. The touch panel driver may output a coordinate and corresponding electrostatic capacitance value for each sensor. The touch panel driver may also output a sensor identifier that may be mapped to a coordinate on the touch panel display screen. Additionally, the touch panel driver and touch panel sensors may detect when an instruction object, such as a finger is within a predetermined distance from an operation surface of the touch panel display screen. That is, the instruction object does not necessarily need to directly contact the operation surface of the touch panel display screen for touch sensors to detect the instruction object and perform processing described herein. For example, in certain embodiments, the touch panel 1244 may detect a position of a user's finger around an edge of the display panel 1243 (e.g., gripping a protective case that surrounds the display/touch panel). Signals may be transmitted by the touch panel driver, e.g. in response to a detection of a touch operation, in response to a query from another element based on timed data exchange, etc.

The touch panel 1244 and the display 1243 may be surrounded by a protective casing, which may also enclose the other elements included in the user device 1234. In certain embodiments, a position of the user's fingers on the protective casing (but not directly on the surface of the display 1243) may be detected by the touch panel 1244 sensors. Accordingly, the controller 1240 may perform display control processing described herein based on the detected position of the user's fingers gripping the casing. For example, an element in an interface may be moved to a new location within the interface (e.g., closer to one or more of the fingers) based on the detected finger position.

Further, in certain embodiments, the controller 1240 may be configured to detect which hand is holding the user device 1234, based on the detected finger position. For example, the touch panel 1244 sensors may detect a plurality of fingers on the left side of the user device 1234 (e.g., on an edge of the display 1243 or on the protective casing) and detect a single finger on the right side of the user device 1234. In this exemplary scenario, the controller 1240 may determine that the user is holding the user device 1234 with his/her right hand because the detected grip pattern corresponds to an expected pattern when the user device 1234 is held only with the right hand.

The operation key 1245 may include one or more buttons or similar external control elements, which may generate an operation signal based on a detected input by the user. In addition to outputs from the touch panel 1244, these operation signals may be supplied to the controller 1240 for performing related processing and control. In certain aspects of the present disclosure, the processing and/or functions associated with external buttons and the like may be performed by the controller 1240 in response to an input operation on the touch panel 1244 display screen rather than the external button, key, etc. In this way, external buttons on the user device 1234 may be eliminated in lieu of performing inputs via touch operations, thereby improving water-tightness.

The antenna 1252 may transmit/receive electromagnetic wave signals to/from other external apparatuses, and the short-distance wireless communication processor 1253 may control the wireless communication performed between the other external apparatuses. Bluetooth, IEEE 802.11, and near-field communication (NFC) are non-limiting examples of wireless communication protocols that may be used for inter-device communication via the short-distance wireless communication processor 1253.

The user device 1234 may include a motion sensor 1254. The motion sensor 1254 may detect features of motion (i.e., one or more movements) of the user device 1234. For example, the motion sensor 1254 may include an accelerometer to detect acceleration, a gyroscope to detect angular velocity, a geomagnetic sensor to detect direction, a geo-location sensor to detect location, etc., or a combination thereof to detect motion of the user device 1234. In certain embodiments, the motion sensor 1254 may generate a detection signal that includes data representing the detected motion. For example, the motion sensor 1254 may determine a number of distinct movements in a motion (e.g., from start of the series of movements to the stop, within a predetermined time interval, etc.), a number of physical shocks on the user device 1234 (e.g., a jarring, hitting, etc., of the electronic device), a speed and/or acceleration of the motion (instantaneous and/or temporal), or other motion features. The detected motion features may be included in the generated detection signal. The detection signal may be transmitted, e.g., to the controller 1240, whereby further processing may be performed based on data included in the detection signal. The motion sensor 1254 can work in conjunction with a Global Positioning System (GPS) section 1248. The information of the present position detected by the GPS section 1248 is transmitted to the controller 1240. An antenna 1247 is connected to the GPS section 1248 for receiving and transmitting signals to and from a GPS satellite.

The user device 1234 may include a camera section 1255, which includes a lens and shutter for capturing photographs of the surroundings around the user device 1234. In an embodiment, the camera section 1255 captures surroundings of an opposite side of the user device 1234 from the user. The images of the captured photographs can be displayed on the display panel 1243. A memory section saves the captured photographs. The memory section may reside within the camera section 1255 or it may be part of the memory 1246.

The camera section 1255 can be a separate feature attached to the user device 1234 or it can be a built-in camera feature.

Figure 13:
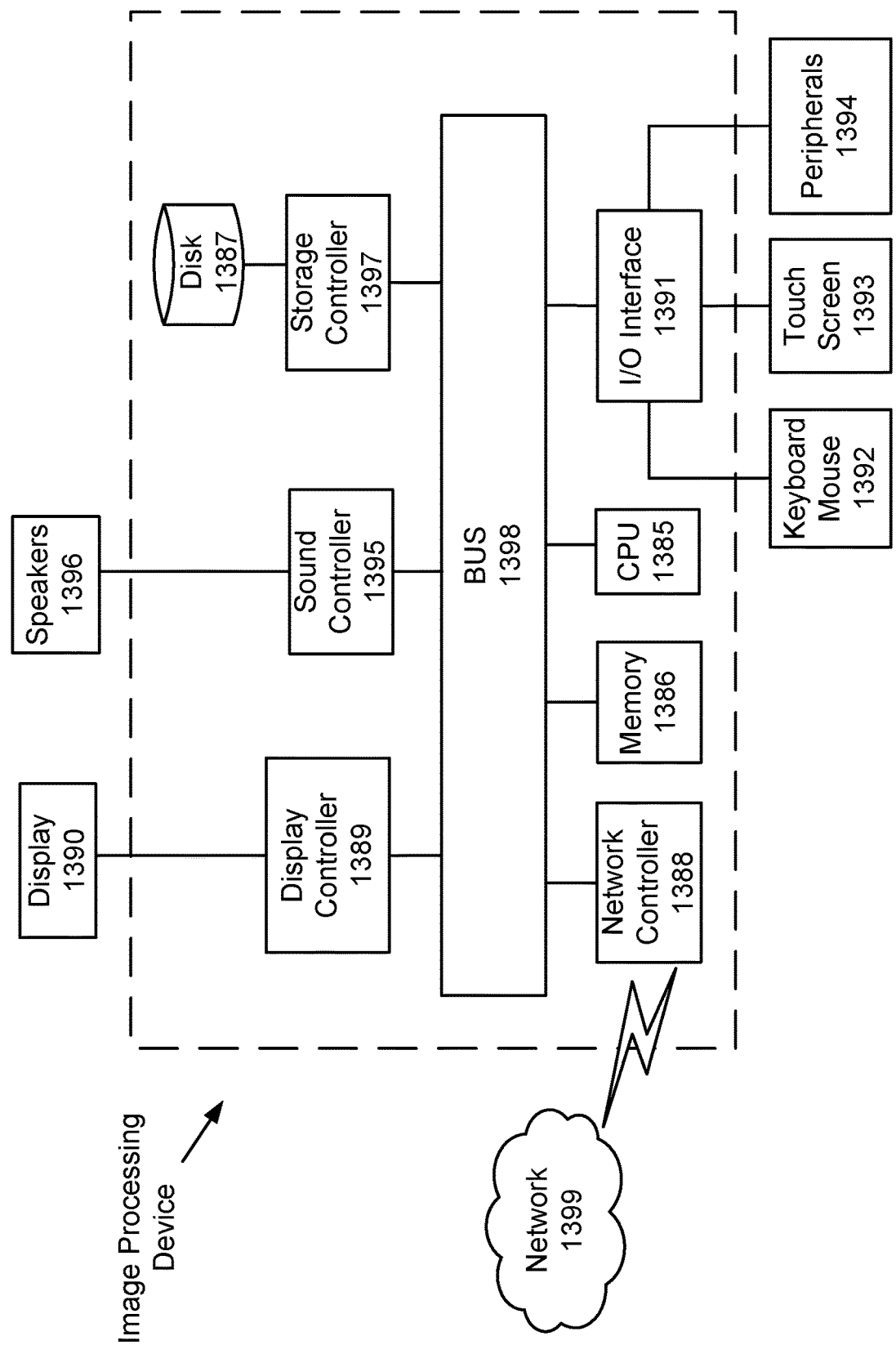
FIG. 13 is a hardware schematic of an image processing device, according to an exemplary embodiment of the present disclosure.

Next, a hardware description of the image processing device according to exemplary embodiments is described with reference to FIG. 13. In FIG. 13, the image processing device includes a CPU 1385 which performs the processes described above. The process data and instructions may be stored in memory 1386. These processes and instructions may also be stored on a storage medium disk 1387 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the head unit communicates, such as a server or computer.

Further, the claimed advancements may be provided as a utility application, background daemon, or component of an operating system, or combination thereof, executing in conjunction with CPU 1385 and an operating system such as MICROSOFT WINDOWS 7, UNIX, SOLARIS, LINUX, APPLE MAC-OS and other operating systems known to those skilled in the art.

The hardware elements in order to achieve the head unit may be realized by various circuitry elements, known to those skilled in the art. For example, CPU 1385 may be a XEON or CORE processor from INTEL of America or an OPTERON processor from AMD of America, or may be other CPU or processor types that would be recognized by one of ordinary skill in the art. Alternatively, the CPU 1385 may be implemented on an FPGA, ASIC, PLD or using discrete logic circuits, as one of ordinary skill in the art would recognize. Further, CPU 1385 may be implemented as multiple processors cooperatively working in parallel to perform the instructions of the inventive processes described above.

The image processing device in FIG. 13 also includes a network controller 1388, such as an INTEL Ethernet PRO network interface card from INTEL Corporation of America, for interfacing with network 1399. As can be appreciated, the network 1399 can be a public network, such as the Internet, or a private network such as an LAN or WAN network, or any combination thereof and can also include PSTN or ISDN sub-networks. The network 1399 can also be wired, such as an Ethernet network, or can be wireless such as a cellular network including EDGE, 3G and 4G wireless cellular systems. The wireless network can also be WIFI, Bluetooth, or any other wireless form of communication that is known.

The image processing device further includes a display controller 1389, such as a NVIDIA GEFORCE GTX or QUADRO graphics adaptor from NVIDIA Corporation of America for interfacing with display 1390, such as a HEWLETT-PACKARD HPL2445w LCD monitor. A general purpose I/O interface 1391 interfaces with a keyboard and/or mouse 1392 as well as a touch screen panel 1393 on or separate from display 1390. General purpose I/O interface also connects to a variety of peripherals 1394 including printers and scanners, such as an OFFICEJET or DESKJET from HEWLETT-PACKARD.

A sound controller 1395 is also provided in the image processing device, such as SOUND BLASTER X-Fi Titanium from CREATIVE, to interface with speakers/microphone 1396 thereby providing sounds and/or music.

The general purpose storage controller 1397 connects the storage medium disk 1387 with communication bus 1398, which may be an ISA, EISA, VESA, PCI, or similar, for interconnecting all of the components of the image processing device. A description of the general features and functionality of the display 1390, keyboard and/or mouse 1392, as well as the display controller 1389, storage controller 1397, network controller 1388, sound controller 1395, and general purpose I/O interface 1391 is omitted herein for brevity as these features are known.

Embodiments of the present disclosure may also be as set forth in the following parentheticals.

(1) An image-guided laryngoscope, comprising a housing having a translational assembly including a motor, the housing configured to hold a display coupled to a proximal end thereof, a primary blade coupled to a distal end of the housing and having a channel, a camera assembly having a camera, an endotracheal tube configured to translate within the channel of the primary blade, and processing circuitry configured to receive images from the camera and to control the translational assembly to translate the endotracheal tube within the channel of the primary blade based on processing the received images, wherein the endotracheal tube is coupled to an endotracheal tube carriage, the endotracheal tube carriage being coupled to the translational assembly, wherein the camera is removably provided within a distal end of the endotracheal tube, the camera being in electrical communication with the processing circuitry, the processing circuitry being configured to transmit image information acquired by the camera to the display.

(2) The image-guided laryngoscope according to (1), wherein the translational assembly further comprises a power supply, a lead screw, and a linear guide, wherein the endotracheal tube carriage is coupled to the lead screw via nut and is rotationally constrained by the linear guide.

(3) The image-guided laryngoscope according to either (1) or (2), wherein the translation of the endotracheal tube within the channel of the primary blade is initiated responsive to a user command via a tactile interface.

(4) The image-guided laryngoscope according to any of (1) to (3), wherein the processing circuitry is further configured to control the translational assembly to translate the endotracheal tube within the channel of the primary blade based upon recognition of an object in the received images.

(5) The image-guided laryngoscope according to any of (1) to (4), wherein the recognition of the object of the received images is based upon a classifier, the classifier being trained to identify one or more biological structures of a laryngotracheal tract.

(6) The image-guided laryngoscope according to any of (1) to (5), wherein the camera assembly further comprises one or more light sources configured to illuminate a laryngotracheal tract.

(7) The image-guided laryngoscope according to any of (1) to (6), further comprising an ancillary blade adjacent to the primary blade.

(8) The image-guided laryngoscope according to any of (1) to (7), wherein the primary blade and a secondary blade have different curvatures.

(9) The image-guided laryngoscope according to any of (1) to (8), wherein the endotracheal tube further comprises an endotracheal tube alignment aid configured to couple with the endotracheal tube carriage and mitigate rotation of the endotracheal tube about an axis of the endotracheal tube.

(10) The image-guided laryngoscope according to any of (1) to (9), wherein the processing circuitry is further configured to control the translational assembly to translate the endotracheal tube within the channel of the primary blade based on a determination of a proximity of one or more biological structures, the determination performed based on information from a tactile sensor disposed within the endotracheal tube.

(11) A method of laryngoscopy via image-guided laryngoscope, comprising receiving, via processing circuitry, images from a camera of a camera assembly, via processing circuitry, processing, via the processing circuitry, the received images, and translating, via the processing circuitry, an endotracheal tube based upon the processing of the received images, the endotracheal tube being configured to translate within a channel of a primary blade, wherein the endotracheal tube is coupled to an endotracheal tube carriage, the endotracheal tube carriage being coupled to a translational assembly, wherein the primary blade is coupled to a distal end of a housing of the image-guided laryngoscope, the housing comprising the translational assembly including a motor and configured to hold a display coupled to a proximal end thereof, wherein the camera is removably provided within a distal end of the endotracheal tube, the camera being in electrical communication with the processing circuitry, the processing circuitry being configured to transmit image information acquired by the camera to the display.

(12) The method according to (11), wherein the translational assembly further comprises a power supply, a lead screw, and a linear guide, wherein the endotracheal tube carriage is coupled to the lead screw via nut and is rotationally constrained by the linear guide.

(13) The method according to either (11) or (12), wherein translating the endotracheal tube within the channel of the primary blade is initiated responsive to a user command via a tactile interface.

(14) The method according to any of (11) to (13), wherein the processing circuitry is further configured to control the translational assembly to translate the endotracheal tube within the channel of the primary blade based upon recognition of an object in the received images.

(15) The method according to any of (11) to (14), wherein the recognition of the object of the received images is based upon a classifier, the classifier being trained to identify one or more biological structures of a laryngotracheal tract.

(16) The method according to any of (11) to (15), wherein the camera assembly further comprises one or more light sources configured to illuminate a laryngotracheal tract.

(17) The method according to any of (11) to (16), wherein the image-guided laryngoscope further comprises an ancillary blade adjacent to the primary blade.

(18) The method according to any of (11) to (17), wherein the primary blade and a secondary blade have different curvatures.

(19) The method according to any of (11) to (18), wherein the endotracheal tube further comprises an endotracheal tube alignment aid configured to couple with the endotracheal tube carriage and mitigate rotation of the endotracheal tube about an axis of the endotracheal tube.

(20) The method according to any of (11) to (19), wherein the processing circuitry is further configured to control the translational assembly to translate the endotracheal tube within the channel of the primary blade based upon a determination of a proximity of one or more biological structures, the determination performed based upon information from a tactile sensor disposed within the endotracheal tube.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An image-guided laryngoscope, comprising:
   a housing having a translational assembly including a motor, the housing configured to hold a display coupled to a proximal end thereof;
   a primary blade coupled to a distal end of the housing and having a channel;
   a camera assembly having a camera;
   an endotracheal tube configured to translate within the channel of the primary blade; and
   processing circuitry configured to receive images from the camera and to control the translational assembly to translate the endotracheal tube within the channel of the primary blade based on processing the received images,
   wherein the endotracheal tube is coupled to an endotracheal tube carriage, the endotracheal tube carriage being coupled to the translational assembly,
   wherein the camera is disposed at a distal end of a camera tube and is removably provided within a distal end of the endotracheal tube, the endotracheal tube surrounding the camera tube, and
   wherein the camera is configured to translate in tandem with translation of the endotracheal tube surrounding the camera tube due to the translational assembly, the camera being in electrical communication with the processing circuitry, the processing circuitry being configured to transmit image information acquired by the camera to the display.

2. The image-guided laryngoscope according to claim 1, wherein the translational assembly further comprises:
   a power supply;
   a lead screw; and
   a linear guide,
   wherein the endotracheal tube carriage is coupled to the lead screw via a nut and is rotationally constrained by the linear guide.

3. The image-guided laryngoscope according to claim 1, wherein the translation of the endotracheal tube within the channel of the primary blade is initiated responsive to a user command via a tactile interface.

4. The image-guided laryngoscope according to claim 1, wherein the processing circuitry is further configured to control the translational assembly to translate the endotracheal tube within the channel of the primary blade based upon recognition of an object in the received images.

5. The image-guided laryngoscope according to claim 4, wherein the recognition of the object of the received images is based upon a classifier, the classifier being trained to identify one or more biological structures of a laryngotracheal tract.

6. The image-guided laryngoscope according to claim 1, wherein the camera assembly further comprises one or more light sources configured to illuminate a laryngotracheal tract.

7. The image-guided laryngoscope according to claim 1, further comprising an ancillary blade adjacent to the primary blade.

8. The image-guided laryngoscope according to claim 1, wherein the primary blade and a secondary blade have different curvatures.

9. The image-guided laryngoscope according to claim 1, wherein the endotracheal tube further comprises an endotracheal tube alignment aid configured to couple with the endotracheal tube carriage and mitigate rotation of the endotracheal tube about an axis of the endotracheal tube.

10. The image-guided laryngoscope according to claim 1, wherein the processing circuitry is further configured to control the translational assembly to translate the endotracheal tube within the channel of the primary blade based on a determination of a proximity of one or more biological structures, the determination performed based on information from a tactile sensor disposed within the endotracheal tube.

11. A method of laryngoscopy via image-guided laryngoscope, comprising:
  receiving, via processing circuitry, images from a camera of a camera assembly;
  processing, via the processing circuitry, the received images; and
  translating, via the processing circuitry, an endotracheal tube based upon the processing of the received images, the endotracheal tube being configured to translate within a channel of a primary blade,
  wherein the endotracheal tube is coupled to an endotracheal tube carriage, the endotracheal tube carriage being coupled to a translational assembly,
  wherein the primary blade is coupled to a distal end of a housing of the image-guided laryngoscope, the housing comprising the translational assembly including a motor and configured to hold a display coupled to a proximal end thereof,
  wherein the camera is disposed at a distal end of a camera tube and is removably provided within a distal end of the endotracheal tube, the endotracheal tube surrounding the camera tube, and
  wherein the camera is configured to translate in tandem with translation of the endotracheal tube surrounding the camera tube due to the translational assembly, the camera being in electrical communication with the processing circuitry, the processing circuitry being configured to transmit image information acquired by the camera to the display.

12. The method according to claim 11, wherein the translational assembly further comprises:
  a power supply;
  a lead screw; and
  a linear guide,
  wherein the endotracheal tube carriage is coupled to the lead screw via a nut and is rotationally constrained by the linear guide.

13. The method according to claim 11, wherein translating the endotracheal tube within the channel of the primary blade is initiated responsive to a user command via a tactile interface.

14. The method according to claim 11, wherein translating the endotracheal tube within the channel of the primary blade is based upon recognition of an object in the received images.

15. The method according to claim 14, wherein the recognition of the object of the received images is based upon a classifier, the classifier being trained to identify one or more biological structures of a laryngotracheal tract.

16. The method according to claim 11, wherein the camera assembly further comprises one or more light sources configured to illuminate a laryngotracheal tract.

17. The method according to claim 11, wherein the image-guided laryngoscope further comprises an ancillary blade adjacent to the primary blade.

18. The method according to claim 11, wherein the primary blade and a secondary blade have different curvatures.

19. The method according to claim 11, wherein the endotracheal tube further comprises an endotracheal tube alignment aid configured to couple with the endotracheal tube carriage and mitigate rotation of the endotracheal tube about an axis of the endotracheal tube.

20. The method according to claim 11, wherein translating the endotracheal tube within the channel of the primary blade is based upon a determination of a proximity of one or more biological structures, the determination performed based upon information from a tactile sensor disposed within the endotracheal tube.

* * * * *